United States Patent [19]

Nohr

[11] Patent Number: 4,921,803
[45] Date of Patent: * May 1, 1990

[54] IMMOBILIZED BLUE-GREEN ALGAE

[75] Inventor: Ronald S. Nohr, Roswell, Ga.

[73] Assignee: Kimberly-Clark Corporation, Neenah, Wis.

[*] Notice: The portion of the term of this patent subsequent to Nov. 7, 2006 has been disclaimed.

[21] Appl. No.: 26,927

[22] Filed: Mar. 17, 1987

[51] Int. Cl.$^5$ .................. C12N 11/12; C12N 11/08; C12M 1/40; C05F 11/08

[52] U.S. Cl. ........................................ 435/179; 71/6; 71/7; 435/177; 435/180; 435/182; 435/257; 435/288

[58] Field of Search .............. 435/257, 180, 177, 182, 435/288; 71/6, 7, 8, 9, 10

[56] References Cited

U.S. PATENT DOCUMENTS

| | | | |
|---|---|---|---|
| 3,115,404 | 12/1963 | Carney | 71/6 |
| 3,168,796 | 2/1965 | Scott et al. | 71/7 X |
| 3,402,103 | 9/1968 | Amberg et al. | 435/842 X |
| 4,155,737 | 5/1979 | Dommergues et al. | 71/6 |
| 4,287,305 | 9/1981 | Compere et al. | 435/180 X |
| 4,578,351 | 3/1986 | Rosevear et al. | 435/41 |
| 4,578,354 | 3/1986 | Cannon | 435/178 |
| 4,774,186 | 9/1988 | Schaefer, Jr. et al. | 435/257 |

OTHER PUBLICATIONS

Kolot, F. B., Process Biochemistry, Aug./Sep. 1981, pp. 2–9.
H. W. Paerl, Can. J. Bot., 60, 2542, (1982).
J. L. Ramos and M. G. Guerrero, Arch. Microbiol., 136, 81, (1983).
J. S. Chapman and J. C. Meeks, J. Bacteriol., 156, 122, (1983).
O. Ito and I. Watanabe, New Phytol., 95, 647, (1983).
W. A. Wurtsbaugh and A. J. Horne, Can. J. Fish. Aquat. Sci., 40, 1419, (1983).
P. M. Mullineaux et al., J. Gen. Microbiol., 129, 1689, (1983).
Y. Chen, Zhiwu Shenglixue Tongxun, 1983, 22.
P. S. Tang et al., in C. K. Tseng, Editor, "Proceedings of the Joint China–U.S. Phycology Symposium," Science Press, Beijing, China, 1983, pp. 339–363.
L. Leonardson, Oecologia, 63, 398, (1984).
R. G. Elder and M. Parker, J. Phycol., 20, 296, (1984).
L. J. Stal et al., Marine Biology, 82, 217, (1984).
B. Bergman et al., Z. Pflanzenphysiol., 113, 451, (1984).
D. H. Turpin et al., Plant Physiol., 74, 710, (1984).
A. Kumar et al., J. Bacteriol., 155, 493, (1983).
G. S. Vankataraman and S. Neelakantan, J. Gen. Appl. Microbiol., 13, 53, (1967).
W. D. P. Stewart et al., in "Nitrogen and Rice," International Rice Research Institute, Los Banos, Laguna, Philippines, 1979, pp. 263–285.
G. S. Venkataraman in "Nitrogen and Rice," International Rice Research Institute, Los Banos, Laguna, Philippines, 1979, pp. 311–321.
A. Agarwal, Nature, 279, 181, (1979).
O. Ito and I. Watanabe, Soil Sci. Plant Nutr., 27, 169, (1981).
G. S. Venkataraman, Current Science, 50, 253, (1981).
G. S. Venkataraman, Trans. Int. Congr. Soil Sci. 12th, 2, 69, (1982).
Z. T. Begum, Bangladesh J. Bot., 12, 127, (1983).
L. Shanghao (S. H. Ley) and W. Qianlin, in C. K.

(List continued on next page.)

Primary Examiner—David M. Naff
Attorney, Agent, or Firm—William E. Maycock

[57] ABSTRACT

A composite is prepared which includes a substantially water-insoluble particulate or fibrous support having a surface energy of at least about 19 dynes per cm to which nitrogen-fixing filamentous heterocystous blue-green algae are attached. The support does not have a deleterious effect on the viability of the attached algae, and is preferably polypropylene or cellulosic. Preparing the composite includes contacting the support with blue-green algae to permit the algae to attach to the support by means of heterocyst cells. The attached cells in a nitrogen-deficient environment, fix nitrogen at a rate substantially greater than unattached cells, and have agricultural applications.

7 Claims, 15 Drawing Sheets

OTHER PUBLICATIONS

Tseng, Editor, "Proceedings of the Joint China-U.S. Phycology Symposium," Science Press, Beijing, China, 1983, pp. 479-496.

A. Islam et al., *Indian J. Agric. Sci.*, 54, 1056, (1984).

V. Rajaramamohan Rao and J. L. N. Rao, *Plant and Soil*, 81, 111, (1984).

B. S. Kundu and A. C. Gaur, *Plant and Soil*, 81, 227, (1984).

I. Watanabe, *Outlook on Agriculture*, 13, (1984).

H. C. Bold and M. J. Wynne, "Introduction to the Algae," Second Edition, Prentice-Hall, Inc., Englewood Cliffs, N.J., 1985, p. 37.

B. R. Schlender, "New Uses for Algae Improve Image of a Lowly Plant Group," *The Wall Street Journal*, Friday, Jul. 11, 1986, p. 25.

*Biotechnology News*, Oct. 9, 1985, p. 6.

E. Eckholm, "Science Tries to Harness Bacterial Overachievers," *The New York Times*, Tuesday, Feb. 24, 1987, p. 15.

W. Zimmerman et al., *Soil Science*, 130, 11, (1980).

A. Muallem, *Biotech 83: Proc. Int. Conf. Commer. Appl. Implic. Biotechnol.*, 1st 1983, pp. 1037-1050.

S. C. Musgrave et al., *Biotechnol. Lett.*, 4, 647, (1982).

S. C. Musgrave et al., *Adv. Ferment. Proc. Conf.*, 1983, pp. 184-190.

M. Potts, *J. Bacteriol.*, 164, 1025, (1985).

K. Venkatasubramanian and Y. Toda, *Biotechnology and Bioengineering Symp.*, No. 10, 237-245, (1980).

H. H. Weetall, "Immobilization by Covalent Attachment and by Entrapment", in R. A. Messing, Editor, Immobilized Enzymes for Industrial Reactors, Academic Press, N.Y., 1975, pp. 99-117.

D. S. Coxson and K. A. Kershaw, *Can. J. Bot.*, 61, 2658, (1983).

S. Scherer et al., *Oecologia*, 62, 418, (1984).

 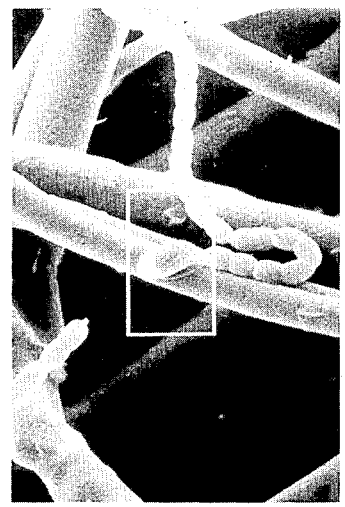
FIG. 7B      FIG. 7A
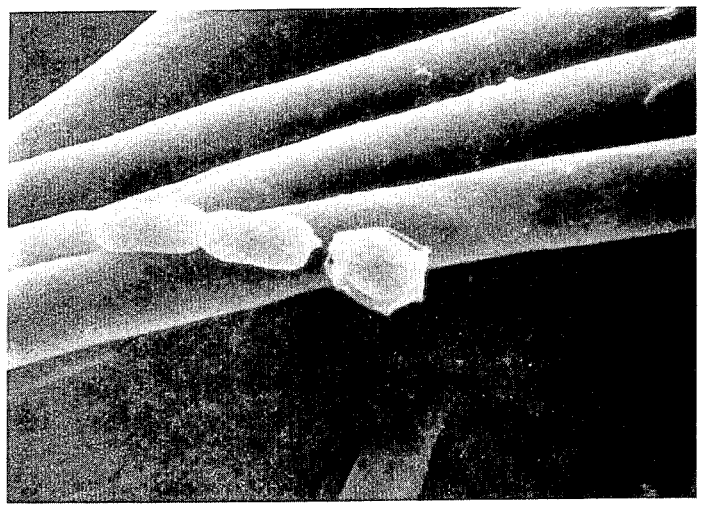
FIG. 8

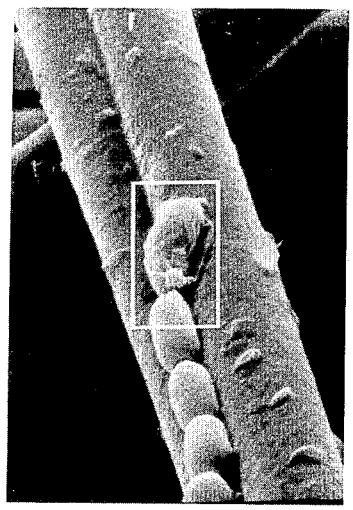
FIG. 9B    FIG. 9A
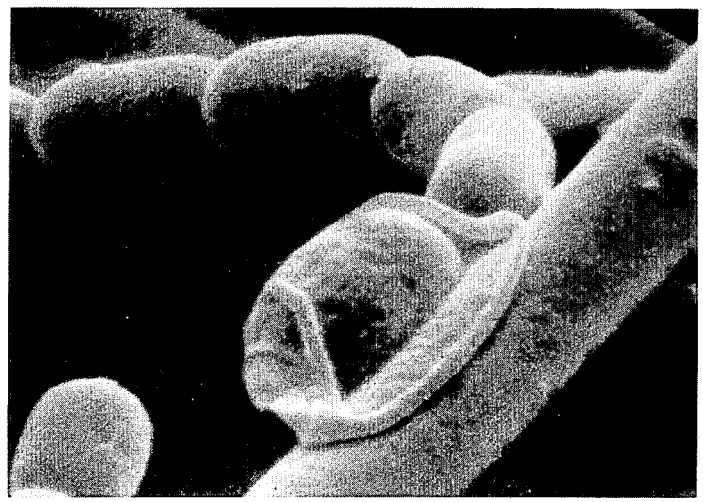
FIG. 10

IMMOBILIZED BLUE-GREEN ALGAE

CROSS-REFERENCES TO RELATED APPLICATIONS

The algae/support composite of the present invention in sheet form is described and claimed in copending and commonly assigned Application Ser. No. 07/027,282, entitled IMMOBILIZED BLUE-GREEN ALGAE IN SHEET FORM and filed of even date in the names of J. Gavin MacDonald, Ronald S. Nohr, and William E. Maycock. A multilayered structure, one component of which is the algae/support composite of the present invention, is described and claimed in copending and commonly assigned Application Ser. No. 07/026,597, entitled MULTILAYERED STRUCTURE INCORPORATING IMMOBILIZED BLUE-GREEN ALGAE THEREIN and filed of even date in the names of J. Gavin MacDonald and Ronald S. Nohr, now U.S. Pat. No. 4,879,232.

BACKGROUND OF THE INVENTION

The present invention relates to immobilized blue-green algae. More particularly, the present invention relates to immobilized blue-green algae having enhanced growth and nitrogen-fixation rates.

In recent years, there has been an increasing interest in the use of biological nitrogen fixation as a replacement for chemical nitrogen fertilizers. However, biological nitrogen fixation can be carried out only by a limited number of microorganisms. Foremost, perhaps, among such microorganisms are the blue-green algae, although not all blue-green algae are capable of fixing nitrogen. Such algae, i.e., the nitrogen-fixing blue-green algae, are able to fix nitrogen in an aerobic environment. Moreover, they are photosynthetic. For examples of references dealing generally with nitrogen fixation by blue-green algae, see H. W. Paerl, *Can. J. Bot.*, 60, 2542 (1982); J. L. Ramos and M. G. Guerrero, *Arch. Microbiol.*, 136, 81 (1983); J. S. Chapman and J. C. Meeks, *J. Bacteriol.*, 156, 122 (1983); O. Ito and I. Watanabe, *New Phytol.*, 95, 647 (1983); W. A. Wurtsbaugh and A. J. Horne, *Can. J. Fish. Aquat. Sci.*, 40, 1419 (1983); P. M. Mullineaux et al., *J. Gen. Microbiol.*, 129, 1689 (1983); Y. Chen, *Zhiwu Shenglixue Tonoxun*, 1983, 22; P. S. Tang et al., in C. K. Tseng, Editor, "Proceedings of the Joint China-U.S. Phycology Symposium," Science Press, Beijing, China, 1983, pp. 339-63; L. Leonardson, *Oecologia*, 63, 398 (1984); R. G. Elder and M. Parker, *J. Phycol.*, 20, 296 (1984); L. J. Stal et al., *Marine Biology*, 82, 217 (1984); B. Bergman et al., *Z. Pflanzenphysiol.*, 113, 451 (1984); and D. H. Turpin et al., *Plant Physiol.*, 74, 701 (1984).

Under conditions of nitrogen deficiency, some of the vegetative cells of the algae differentiate into heterocysts which are capable of fixing atmospheric nitrogen. See, by way of illustration only, A. Kumar et al., *J. Bacteriol.*, 155, 493 (1983); M. Roussard-Jacquemin, *Can. . Microbiol.*, 29, 1564 (1983); and references cited therein.

The use of blue-green algae as a biological nitrogen fertilizer is, of course, known. Such algae have been studied for or used in the cultivation of rice; see, e.g., G. S. Vankataraman and S. Neelakantan, *J. Gen. Aool. Microbiol.*, 13, 53 (1967); W. D. P. Stewart et al., in "Nitrogen and Rice," International Rice Research Institute, Los Banos, Laguna, Philippines, 1979, pp. 263-85; G. S. Venkataraman in "Nitrogen and Rice," International Rice Research Institute, Los Banos, Laguna, Philippines, 1979, pp. 311-21; A. Agarwal, *Nature*, 279. 181 (1979); O. Ito and I. Watanabe, *Soil Sci. Plant Nutr.*, 27, 169 (1981); G. S. Venkataraman, *Current Science*, 50, 253 (1981); G. S. Venkataraman, *Trans. Int. Conor. Soil Sci. 12th*, 2, 69 (1982); Z. T. Begum, *Bangladesh J. Bot.*, 12, 127 (1983); L. Shanghao (S. H. Ley) and W. Qianlin, in C. K. Tseng, Editor, "Proceedings of the Joint China-U.S. Phycology Symposium," Science Press, Beijing, China, 1983, pp. 479-96; A. Islam et al., *Indian J. Agric. Sci.*, 54, 1056 (1984); V. Rajaramamohan Rao and J. L. N. Rao, *Plant and Soil*, 81, 111 (1984); B. S. Kundu and A. C. Gaur, *Plant and Soil*, 81, 227 (1984); I. Watanabe, *Outlook on Agriculture*, 13, pages unknown (1984); and H. C. Bold and M. J. Wynne, "Introduction to the Algae," Second Edition, Prentice-Hall, Inc., Englewood Cliffs, N.J., 1985, p. 37.

In addition, at least one company is marketing a blue-green algal fertilizer for the lawn and garden market. The fertilizer is prepared by blending dried algae with a soil-like carrier which allegedly prevents the dormant algae from dying. See B. R. Schlender, "New Uses for Algae Improve Image of a Lowly Plant Group," *The Wall Street Journal*, Friday, July 11, 1986, p. 25; *Biotechnology News*, Oct. 9, 1985, p. 6; and E. Eckholm, "Science Tries to Harness Bacterial Overachievers," *The New York Times*, Tuesday, Feb. 24, 1987, p. 15. Moreover, the application of blue-green algae to tomato plants reportedly resulted in 45% more growth (weight gain) than plants treated with the same amount of commercial fertilizer. It was postulated that the weight gain may be due to the secretion of a plant-growth hormone (Science/Technology Concentrates, *Chemical and Engineering News*, date unknown). Interestingly, cultivated soils apparently contain inconsequential numbers of blue-green algae; see W. Zimmerman et al., *Soil Science*, 130, 11 (1980).

In contrast with the large number of studies on the fixation of nitrogen by blue-green algae and the use of blue-green algae as a nitrogen fertilizer, little work apparently has been done with immobilized blue-green algae. Moreover, what work has been carried out was done primarily with entrapped cells, as described in the paragraphs which follow.

According to A. Muallem, *Biotech 83: Proc. Int. Conf. Commer. Appl. Implic. Biotechnol. 1 st* 1983, pp. 1037-50, seven species of cyanobacteria, or blue-green algae, were entrapped in polyurethane foams. The entrapped cells, however, were used for the long-term photoproduction of hydrogen and NADPH$_2$ from ascorbate and water. To immobilize the algal cells, pieces of foam were added to the culture vessels before autoclaving and inoculating with the algae. One species did not remain entrapped in any foam. In at least some cases, freeze-thaw cycles were employed as part of the immobilization procedure. The reference includes one electron micrograph, regarding which it was reported that short filaments and single cells were seen adhering to the polyurethane fibers which constitute the pore walls, and that cell envelope components were solely responsible for cell hydrophobicity which plays the major role in adhesion of benthic cyanobacteria on solid surfaces which have little or no surface charge. It is clear that no effort was made to measure nitrogen fixation by the immobilized algae. The immobilized cells apparently did not grow since they did not undergo any regenerative carbon metabolism.

Whole filaments of a nitrogen-fixing cyanobacterium were immobilized by entrapment in calcium alginate gel beads; S. C. Musgrave et al., *Biotechnol. Lett.*, 4, 647 (1982) and *Adv. Ferment. Proc. Conf.* 1983, pp. 184–90. The immobilized cyanobacterium were used in various continuous-flow reactors for the sustained production of ammonia.

Finally, protein turnover in immobilized cells of a cyanobacterium was studied by M. Potts, *J. Bacteriol.*, 164, 1025 (1985). The cells were immobilized by transfering a sample of a cell suspension to Whatman 3MM filter discs (23-mm diameter) which were supported on steel pins. The study employed only 50-microliter samples of a well-dispersed cell suspension and the algal filaments reportedly were immobilized immediately within the confines of the upper matrix of the support, occupying a circular area approximately 8 mm in diameter. The immobilization appears to be primarily an entrapment, and nitrogen fixation by the cells was not studied.

While blue-green algae were not involved, it perhaps should be mentioned that the continuous production of ammonia by an immobilized nitrogen-fixing-system depressed mutant strain of a bacterium, *Klebsiella pneumoniae*, has been reported; K. Venkatasubramanian and Y. Toda, *Biotechnology and Bioengineering Symp. No.* 10, 237–45 (1980). Immobilization involved mixing the cells with a collagen dispersion, adjusting the pH, casting a membrane, and crosslinking it with a mild solution of glutaraldehyde. Thus, the cells were entrapped in a collagen membrane.

SUMMARY OF THE INVENTION

It now has been discovered, quite unexpectedly, that certain nitrogen-fixing blue-green algae, when immobilized, demonstrate either substantially unimpaired viability or significantly enhanced growth and nitrogen-fixation rates compared to algae growing in suspension.

It therefore is an object of the present invention to provide immobilized nitrogen-fixing blue-green algae.

Another object of the present invention is to provide immobilized nitrogen-fixing blue-green algae having significantly enhanced growth and nitrogen-fixation rates in relation to algae growing in suspension.

A further object of the present invention is to provide a composite of a substantially water-insoluble support to which nitrogen-fixing blue-green algae are attached.

Still another object of the present invention is to provide a method of preparing a composite of a substantially water-insoluble support to which nitrogen-fixing blue-green algae are attached.

Yet a further object of the present invention is to provide an agricultural, nutrient-producing composite of a substantially water-insoluble support to which nitrogen-fixing blue-green algae are attached.

These and other objects will be readily apparent to those having ordinary skill in the art from a reading of the specification and claims which follow.

Accordingly, the present invention provides a composite which comprises a substantially water-insoluble support having a surface energy of at least about 19 dynes per cm to which nitrogen-fixing filamentous heterocystous blue-green algae are attached, said support being substantially free of substances which have a significant deleterious effect on the viability of the attached algae.

In preferred embodiments, the algae are attached to the support by means of the algal heterocyst cells.

The present invention also provides a method of preparing a composite comprising a substantially water-insoluble support having a surface energy of at least about 19 dynes per cm to which nitrogen-fixing filamentous heterocystous blue-green algae are attached, said support being substantially free of substances which have a significant deleterious effect on the viability of the attached algae and said algae being attached to said support by means of the algal heterocyst cells, which method comprises contacting said support with an aqueous suspension of said nitrogen-fixing blue-green algae for a time and under conditions sufficient to permit said blue-green algae to attach to said support.

In certain preferred embodiments, the support is either particulate or fibrous and the surface energy of the support is in the range of from about 19 to about 120 dynes per cm. In other preferred embodiments, the surface energy of the support is in the range of from about 30 to about 115 dynes per cm. In still other preferred embodiments, the surface energy of the support is in the range of from about 65 to about 115 dynes per cm.

The present invention further provides an agricultural, nutrient-producing composite which comprises a substantially water-insoluble support having a surface energy of at least about 19 dynes per cm to which nitrogen-fixing filamentous heterocystous blue-green algae are attached, said support being substantially free of substances which have a significant deleterious effect on the viability of the attached algae.

The composite of the present invention is useful as a nitrogen fertilizer in commercial agricultural and home gardening applications, which applications include, by way of illustration only, the use of the composite as a nitrogen fertilizer for agricultural crops, home gardens, and plants growing in greenhouses and such indoor sites as homes, offices, and the like. The composite of the present invention should prove especially useful either as an agricultural product per se or as a component of other agricultural products, such as vegetable row covers and hydroseeding mixtures, to name but a few.

BRIEF DESCRIPTION OF THE DRAWINGS

FIGS. 3–17, inclusive, are reproductions of scanning electron micrographs at varying degrees of magnification of blue-green algae attached to a variety of supports, i.e., of various of the algae/support composites of the present invention.

DETAILED DESCRIPTION OF THE INVENTION

Figure 1:
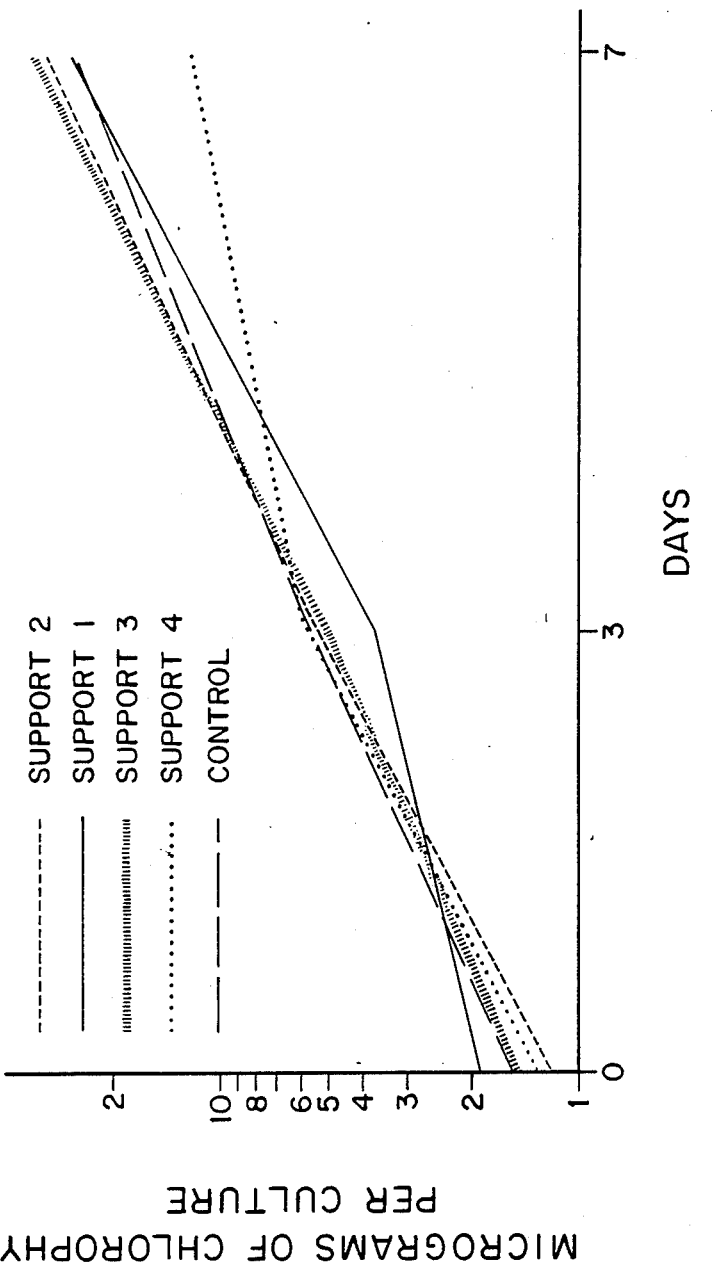
FIG. 1 is a plot of algal growth on each of four different supports and in a control culture, all in a liquid medium, against time.

Although the term "immobilized" has been used rather broadly in the prior art, such term is used herein more narrowly. As applied to the composite of the present invention, the term is meant to be essentially synonymous with "attached" and is intended to exclude entrapped algal cells. However, the nature of the attachment is not critical, although the algae preferably are attached by means of the heterocyst cells.

As used herein with reference to nitrogen-fixing filamentous heterocystous blue-green algae, the term "viable" or a variation thereof means simply that the growth and nitrogen-fixing characteristics of the immobilized algae are substantially unimpaired when compared to such characteristics of the same algae in suspension.

In general, the use of any nitrogen-fixing filamentous heterocystous blue-green algae comes within the spirit and scope of the present invention. Such algae are chlorophyllous prokaryotic organisms which can be classified by either of two systems. The first system is a taxonomic classification described by T. V. Desikachary in a chapter entitled "Classical Taxonomy," in N. G. Carr and B. A. Whitton, Editors, "The Biology of Blue-Green Algae," University of California Press, Berkeley, 1973, pp. 473–481. According to this system, the nitrogen-fixing filamentous heterocystous blue-green algae in general are those which fall within the following families and genera:

| Order | Family | Genus |
|---|---|---|
| Nostocales | Oscillatoriaceae | Arthrospira |
| | | Borzia |
| | | Crinalium |
| | | Gomontiteilla |
| | | Isocystis |
| | | Lyngbya |
| | | Microcoleus |
| | | Oscillatoria |
| | | Phormidium |
| | | Schizothrix |
| | | Spirulina |
| | | Symploca |
| | Nostocaceace | Anabeana |
| | | Anabaenopsis |
| | | Aphanizomenon |
| | | Aulosira |
| | | Camptylonemopsis |
| | | Cylindrospermum |
| | | Hormothamnion |
| | | Nostoc |
| | | Raphidiopsis |
| | | Richelia |
| | | Wollea |
| | Scytonemataceae | Coleodesmium |
| | | Hydrocoryne |
| | | Scytonema |
| | | Scytonematopsis |
| | | Tolypothrix |
| | Microchaetaceae | Fortiea |
| | | Michrochaete |
| | Rivulariaceae | Calothrix |
| | | Dichothrix |
| | | Gloeothrichia |
| | | Hammatoidea |
| | | Homoeothrix |
| | | Kyrtuthrix |
| | | Rivularia |
| Stigonematales | Capsosiraceae | Capsosira |
| | | Hyphomorpha |
| | | Loriella |
| | | Pulvinularia |
| | | Stauromatonema |
| | Nostochopsidaceae | Mastigocoleus |
| | | Nostochopsis |
| | Mastigocladaceae | Brachytrichia |
| | | Iyengariella |
| | | Mastigocladus |
| | Stigonemataceae | Doliocatella |
| | | Fischerella |
| | | Geitleria |
| | | Hapalosiphon |
| | | Schmidleinema |
| | | Stigonema |
| | | Westiella |
| | | Westiellopsis |

The second classification system is that described by R. Rippka et al., in "Generic Assignments, Strain Histories and Properties of Pure Cultures of Cyanobacteria," *Journal of General Microbiology*, 111, 1–61 (1979). In that system, all of the nitrogen-fixing filamentous heterocystous species are members of Sections IV and V and comprise species in the following genera:

| Section | Genus |
|---|---|
| IV | Anabeana |
| | Nodularia |
| | Cylindrospermum |
| | Nostoc |
| | Scytonema |
| | Calothrix |
| V | Chlorogloeopsis |
| | Fischerella |

The above-described classification systems are given by way of illustration only, however, and are not to be construed as in any way limiting either the spirit or the scope of the present invention. That is, any filamentous heterocystous blue-green algae which is capable of attaching to or being immobilized on a support and which fixes nitrogen in such attached or immobilized state is deemed to come within the scope of the present invention, whether or not such algae fit either or both of the foregoing classification systems. Thus, such algae include unclassified algae, algae which do not fit either of the foregoing classification systems, algae which are mutants of known algae, algae which have been subjected to gene manipulation procedures, and the like. Moreover, the term "filamentous heterocystous blue-green algae" also is deemed to include organisms which, while perhaps not properly classified as algae, exhibit the nitrogen-fixing and support-attaching characteristics described herein, such as may be derived The nitrogen-fixing filamentous heterocystous blue-green algae grow as chains of cells or filaments. Generally, the filaments are composed of uniform small cells, known as vegetative cells, which grow and divide within the filament. As the length of each filament increases, it becomes more susceptible to shear forces in the environment which cause the filament to break. Each fragment then continues to grow independently. The average filament length thus tends to remain relatively constant as the total number of cells increases.

When cells are grown under conditions which induce nitrogen fixation, i.e., growth in a nitrogen-limited environment, some of the vegetative cells in the filament differentiate to form larger, specialized cells, called heterocysts. The heterocysts are known to be the actual sites of nitrogen fixation. On the average, about one in every 20 to 50 cells develops into a heterocyst. The heterocysts produce fixed nitrogen, i.e., one or more water-soluble nitrogen-containing compounds which can be utilized by plants, which is transferred to the vegetative cells, while the vegetative cells in turn supply energy and carbon compounds to the heterocysts. Excess fixed nitrogen produced by the heterocysts is secreted from the filament, although it is not known whether the actual site of secretion is the heterocyst or the adjacent vegetative cells.

In general, the substantially water-insoluble support to which the nitrogen-fixing filamentous heterocystous blue-green algae are attached to give the composite of the present invention can be any material which has a surface energy of at least about 19 dynes per cm. As will be shown hereinafter, such algae will attach, although to a relatively small extent, to supports having a surface energy as low as about 19 dynes per cm. However, the extent of attachment increases when supports having higher surface energies are employed. In fact, the extent of attachment appears to be directly proportional to the surface energy of the support. Because algae have been observed to attach to supports having surface energies from about 19 to around 115–120 dynes per cm, the support preferably will have a surface energy of from about 19 to about 120 dynes per cm. More preferably, the support will have a surface energy of from about 30 to about 115 dynes per cm and most preferably from about 65 to about 115 dynes per cm.

As already stated, the support should be substantially free of substances having a significant deleterious effect on the viability of the attached algae. Because of the wide variety of supports which can be employed in the present invention, it is not practical to list such substances which may be either naturally occuring in the support or added as a result of manufacturing or processing requirements. However, those having ordinary skill in the art will know of substances and conditions which are harmful to algae, such as extremes in pH, chemicals which are toxic to the algae, and the like. For example, unprocessed pine particles or fibers will kill the nitrogen-fixing filamentous heterocystous bluegreen algae. However, if the wood fibers are processed to remove the deleterious substances, such as during the preparation of a thermomechanical wood pulp, the algae will attach to them. Another example of supports having deleterious substances associated therewith are various woven and nonwoven fabrics which have either in or on the fibers various compounds employed as sizes, lubricants, preservatives, and the like, many of which are extremely difficult to remove from the fabric.

Thus, the support can be a natural, modified natural, or synthetic material. Moreover, the support can be any shape, such as particulate, granular, spherical, fibrous, and the like. The support can be a three-dimensional shaped article, such as a tube, rod, sheet, and the like. The support can be porous or nonporous. If a sheet, the support can be a film or a web, such as a fibrous nonwoven web.

As a practical matter, relatively high surface area supports are preferred since the greater the number of cells per unit volume, the greater the production of fixed nitrogen compounds. Consequently, particulate and fibrous supports are most preferred.

Examples of suitable supports include, among others, poly(tetrafluoroethylene), polymers of perfluoroethylenes having fewer than four fluorine atoms per ethylenic molecule, glass, polyolefins, polyolefins having chemically modified surfaces, polyesters, polyamides, and cellulosics.

For the purposes of the present disclosure, the term "polyolefin" is meant to include any polymeric material a major constituent of which, i.e., at least 50 percent by weight, is a polyolefin. Thus, the term includes homopolymers, copolymers, and polymer blends.

Copolymers can be random or block copolymers of two or more polyolefins (or of two or more different polyolefin monomeric precursers) or of one or more polyolefins and one or more nonpolyolefin polymers. Similarly, polymer blends can utilize two or more polyolefins or one or more polyolefins and one or more nonpolyolefin polymers. As a practical matter, homopolymers and copolymers and polymer blends involving only polyolefins are preferred, with homopolymers being most preferred.

Examples of polyolefins include polyethylene, polystyrene, poly(vinyl chloride), poly(vinyl acetate), poly(vinylidene chloride), poly(acrylic acid), poly(methacrylic acid), poly(methyl methacrylate), poly(ethyl acrylate), polyacrylamide, polyacrylonitrile, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, and the like.

The preferred polyolefins are those prepared from unsaturated hydrocarbon monomers, with polyethylene and polypropylene being most preferred.

As used herein, the term "cellulosic" is meant to include any material a major constituent of which, i.e., at least 50 percent by weight, is cellulose or a cellulose derivative. Thus, the term includes cotton, cellulose acetate, cellulose triacetate, rayon, thermomechanical wood pulp, chemical wood pulp, debonded chemical wood pulp, milkweed, and the like. The preferred cellulosics are the various wood pulps, the preparations of which are well known to those having ordinary skill in the art.

The preferred support materials are polyolefins, surface-modified polyolefins, and cellulosics, with the polyolefins and cellulosics being more preferred. The most preferred support materials are cellulosics.

As already stated, it is necessary that the support be substantially free of substances having a significant deleterious effect on the viability of the attached algae.

The composite of the present invention is readily prepared by simply contacting the chosen support with an aqueous suspension of the blue-green algae for a time and under conditions sufficient to permit the blue-green algae to attach to the support. Typically, the algae will be suspended in the aqueous medium in which they were being grown. However, the use of an aqueous growth medium is not known to be essential. For example, the algae could be grown in a suitable medium, harvested by known techniques, and resuspended in a different aqueous medium. Alternatively, dry support and dry algae can be admixed and then contacted with water or otherwise moistened.

The attachment of the algal cells to the support preferably is by means of the heterocysts. However, attachment of algae to supports by means other than the heterocysts is possible. For example, the cells could be bound to the support by means of chemical binding agents which have two reactive ends, one end being reactive to functional groups present in the sheaths of the cells and the other end being reactive to functional groups at the surface of the support. For illustrations of the kinds of chemistries involved, see, for example, H. H. Weetall, "Immobilization by Covalent Attachment and by Entrapment," in R. A. Messing, Editor, "Immobilized Enzymes for Industrial Reactors," Academic Press, N.Y., 1975, pp.99–117 (although enzymes were involved, the chemistries described generally are applicable to cells, except where the support itself is proteinaceous).

Because the immobilized algae remain viable, the composite of the present invention is especially useful for the production of nutrients, e.g., soluble nitrogen-containing compounds, for a wide variety of growing plants. Thus, the composite can be applied in continuous (sheet-like) or discontinuous form on the soil surrounding a plant to act as a nitrogen fertilizer. Continuous forms of the composite include sheets and rolls, with the latter being especially useful for crops planted in long rows. Discontinuous forms, such as are obtained through the use of supports in particulate or fibrous forms, are perhaps more readily adapted to commercial applications since the composite can be broadcast over a field by already-available equipment. Discontinuous forms also are ideally suited for incorporation into other agricultural products, such as fertilizers, mulches, ground covers, row covers, hydro-seeding mixtures, seed-containing products, and the like. An example of a seed-containing product is a paper or peat tray having a plurality of valleys or depressions in which seeds have been placed. The seeds then are covered with a composite of the present invention or a layer of soil and then a layer of the composite. The tray is simply placed on the soil in a suitable location and watered. As the seeds germinate, the roots penetrate the bottom of the tray and enter the soil. The composite remains on the top of the soil to provide nutrients. Alternatively, the composite can be employed as an aqueous slurry or suspension comprising a mixture of water and a composite of the present invention. Such use, of course, is of significance for hydroseeding procedures since the composite of the present invention not only provides nutrients for the seedlings as they grow but also acts as a protective covering until the soil has been stabilized by the growing plants.

The present invention is further described by the experimental studies which are described below. The studies were carried out in the facilities of the Department of Genetics of Iowa State University, Ames, Iowa. For convenience in presenting them, such studies are not labeled as "Examples", although they are equivalent thereto. Such studies are not to be construed as limiting either the spirit or scope of the present invention.

EXPERIMENTAL STUDIES

All of the experimental studies describe herein were carried out with *Nostoc muscorum* strain 2209 which was obtained from the Culture Collection of Algae at the University of Texas, Austin, Texas. This strain is believed to be representative of the blue-green algae coming within the scope of the present invention. Moreover, the strain grows well in the laboratory and has been characterized physiologically to some extent. It is a good nitrogen fixer and is able to sustain growth supported by nitrogen fixation indefinitely. Finally, related strains of blue-green algae have been found in a variety of habitats, including the soil surfaces of grasslands. Thus, the strain also appears to be a good representative of a class of blue-green algae adapted for growth under conditions similar to those envisioned for the use of the immobilized blue-green algae of the present invention as a nitrogen fertilizer.

The algal cells used in the experimental studies were grown under standard conditions using a completely defined liquid growth medium which contained mineral salts, either with or without soluble nitrogen as required. The medium contained the components given in Table 1, dissolved in double distilled water in the amounts indicated per liter of solution (see M. M. Allen, *Journal of Phycology*, 4, 1-4 (1968):

TABLE 1

| Components of Growth Medium Solution | |
|---|---|
| Compound | Concentration per liter |
| Potassium phosphate | 0.040 g |
| Magnesium sulfate | 0.075 g |
| Calcium chloride | 0.036 g |
| Citric acid | 0.006 g |
| Ferric citrate | 0.006 g |
| Disodium EDTA[a] | 0.001 g |
| Sodium carbonate | 0.020 g |
| Boric acid | 2.86 mg |
| Manganese (II) chloride | 1.81 mg |
| Zinc sulfate | 0.22 mg |
| Sodium molybdate | 0.39 mg |
| Cupric sulfate | 0.08 mg |
| Cobalt (II) nitrate | 0.05 mg |

[a]Disodium ethylenediaminetetraacetic acid

When the presence in the medium of soluble nitrogen was required, sodium nitrate at a concentration of 1.500 g per liter of medium was included as a component.

Depending upon the number of algal cells required, cultures of *Nostoc muscorum* strain 2209 were grown in suspension at any one of three levels. In level 1 cultures, the cells were grown in 50 ml of medium in 250-ml Pyrex ® Erlenmeyer flasks. The cultures were grown under continuous illumination at 30 degrees C. in a Model G-27 PsycroTherm ™ Controlled Environment Incubator Shaker (New Brunswick Scientific Co., Inc., Edison, N.J.). The cultures were aerated by shaking at 125 rpm.

Level 2 cultures were grown in an Airlift Fermenter having a 2-liter capacity (Bethesda Research Laboratories, Gaithersburg, Md.), typically at 30 degrees C.

At level 3, each culture was grown in approximately four liters of medium in a 4-liter Pyrex ® Erlenmeyer flask. The culture was stirred magnetically with a Thermolyne Nuova II Stirrer (Sybron Corporation, Fisher Catalog No. 11-496-60, Fisher Scientific, Pittsburgh, Penna.). Aeration was accomplished by bubbling prehumidified, filtered air through the suspension of algal cells. Air filtration was accomplished by means of a Gelman Bacterial Air Vent (No. 4210, Gelman Instrument Co., Fisher Catalog No. 09-730-125, Fisher Scientific, Pittsburgh, Penna.) between the prehumidifier and the culture flask. Illumination was provided by several 15 watt cool white fluorescent lamps having a length of at least about 44 cm and located on two or more sides of the culture flask. The culture solution was at ambient temperature, usually 22-25 degrees C.

Experiments which required growth on a solid surface utilized liquid medium solidified or gelled with 1 percent by weight Difco Bacto ™ Agar (Difco Laboratories, Fisher Catalog No. DF014001-0, Fisher Scientific, Pittsburgh, Penna.). Fifty-ml aliquots of the agar-containing liquid medium were placed in FISHER-brand ™ 100×15 mm standard presterilized Petri dishes (Fisher Catalog No. 085713, Fisher Scientific, Pittsburgh, Penna.) and allowed to solidify or gel. After innoculating with the desired algal cells, the cultures on agar medium were maintained at 30 degrees C. under continuous illumination in a Precision Illuminated Incubator (GCA Corporation, Fisher Catalog No. 11-67956, Fisher Scientific, Pittsburgh, Penna.). For convenience, the agar-solidified medium is referred to on occasion hereinafter by the letters "ASM".

Most of the cultures were carried out with medium which did not contain soluble nitrogen in order to stimulate the differentiation of vegetative cells into heterocysts and to require the algae to grow under nitrogen-fixing conditions. In some of the initial experiments, however, some cultures employed nitrogen-containing medium in order to evaluate the effect of the absence of heterocysts on immobilization of the algal cells on the supports studied.

When cultures of algae were grown in the presence of a support, each support which was available as a nonwoven web was used in the form of 5-cm diameter disks for both agar medium and level 1 cultures. All other supports were used in amounts which gave a total mass of about 0.05 g per culture; this amount was estimated to have approximately the same effective surface area as the circular samples of nonwoven webs. Unless stated otherwise, each support was sterilized prior to use by steam autoclaving at 20 psig steam pressure and a temperature of 120 degrees C. for 30 minutes.

Immobilization experiments, as already noted, employed level 1 cultures without the need to harvest cells. Experiments which required larger numbers of cells than were present in the level 1 cultures, such as the greenhouse studies, generally involved cells which had been harvested from level 3 cultures. Level 3 cultures were inoculated with a level 2 culture which in turn was inoculated with a level 1 culture.

The harvesting of cells from a level 3 culture generally was accomplished by centrifuging the cells in 250-ml Nalgene centrifuge bottles (Nalge Co., Fisher Catalog No. 05-562-23, Fisher Scientific, Pittsburgh, Penna.) at 1400×G (10,000 rpm) for ten minutes in a Sorvall® Model GS-A rotor in a Sorvall® Superspeed Model RC2-B Automatic Refrigerated Centrifuge (Ivan Sorvall, Inc., Newtown, Conn.). The wet weight of each cell pellet was determined using a Mettler Model PE 2000 Electronic Balance (Mettler Instrument Corporation, Hightstown, N.J.) The supernatant in each bottle was discarded. The cell pellets were resuspended in a small amount of nitrogen-free medium and pooled. The pooled cells then were washed by centrifugation as before and resuspended in fresh nitrogen-free medium.

Because it is not possible to determine the growth rates of filamentous blue-green algae by directly measuring cell numbers, growth rates were determined by measuring the total chlorophyll content of each culture. The concentration of chlorophyll per cell is known to be relatively constant, even under different growth conditions. Thus, the chlorophyll content of a culture is directly proportional to the number of cells present. While under some conditions total protein content also is directly proportional to the number of cells present, the amount of protein per cell varies greatly between vegetative cells and heterocysts and can also vary with changes in the growth rate of the culture. Consequently, total protein content was not deemed to be an appropriate measure of cell numbers and growth rates.

To measure chlorophyll content, cells were harvested from an aliquot of each culture. The chlorophyll in the harvested cells was extracted with 90 percent acetone. In experiments where the ratio of bound (attached) to unbound cells was to be measured, the support with attached cells (if any) was removed from the culture first and the remaining cells were collected by vacuum filtration on a BA-85 0.45 micron filter (Schleicher and Schuell, Inc., Keene, New Hampshire). The support and the thus collected unbound cells were placed in separate 50-ml Nalgene TM polyallomer Oak Ridge centrifuge tubes (Nalge Co., Fisher Catalog No. 05-529-1D, Fisher Scientific, Pittsburgh, Penna.); 10 ml of 90 percent acetone was added to each tube. Each tube then was vortexed for 30 seconds with a Model K-500-4 Vortex Test Tube Mixer (Scientific Instruments, Inc., Springfield, Mass.) and incubated in the dark for 15 minutes. Cell debris, and support when present, were pelleted by centrifuging each tube at 12,000 × g for 10 minutes at 4 degrees C. in a Sorvall® Superspeed RC2-B Automatic Refrigerated Centrifuge fitted with an SS-34 rotor. The supernatant was decanted from the pellet and analyzed spectrophotometrically at 664 and 647 nanometers in a Beckman Model DU-6 single beam spectrophotometer (Beckman Instruments, Inc., Irvine, Calif.). The chlorophyll content of each sample in micrograms (Chl) then was calculated in accordance with the following equation:

$$\text{Chl (g/sample)} = [(A_{664} \times 11.93) - (A_{647} \times 1.93)] \times 10$$

In experiments involving the determination of nitrogen fixation activity, all of the cells were harvested together and the total chlorophyll content was determined for the entire culture. Chlorophyll determinations for the plate growth experiments, i.e., growth on a solid, were carried out in a similar manner, except that the cells were harvested by wiping or scraping them from the agar surface and then transferring them to Oak Ridge centrifuge tubes.

Nitrogen fixation activity was measured by the acetylene reduction technique (see, e.g., R. C. Burns and R. W. F. Hardy, "Nitrogen Fixation in Bacteria and Higher Plants," Springer-Verlag, Berlin, 1975, pp. 10-12). Nitrogenase, the enzyme responsible for the nitrogen-fixing ability of the filamentous heterocystous blue-green algae, also is able to convert acetylene to ethylene, both of which are gases and readily measured quantitatively by GLC (gas-liquid chromatography). Briefly, the nitrogen-fixing activity of a liquid culture was determined by capping the growth flask with a gas-tight rubber septum and injecting into the flask 25 ml of acetylene (Air Products, Allentown, Penna.). The flask was swirled to thoroughly mix the injected acetylene with the resident gas phase. A 10-microliter sample of the mixed gas phase was withdrawn from the flask by means of a Type 701-RN Hamilton syringe (Hamilton Co., Fisher Catalog No. 14-824-3, Fisher Scientific, Pittsburgh, Penna.) fitted with a 26S-gauge Hamilton No. 80427 needle (Hamilton Co., Fisher Catalog No. 14824-9A, Fisher Scientific, Pittsburgh, Penna.). The gas sample thus collected was analyzed on a Carle Model AGC-211 gas chromatograph (Carle Instruments, Inc., Anaheim, Calif.) with a 10 percent by weight Carbowax 20M on a Chromosorb W-HP column (Carle Instruments, Inc.) operating at 200 degrees C. and having a flame ionization detector attached to a Houston Instruments Omniscribe recorder (Houston Instruments, Austin, Tex.). The capped growth or culture flask then was incubated under standard growth conditions and the gas phase was sampled at thirty-minute intervals for two hours. The relative amounts of acetylene and ethylene in each sample were determined by known procedures from the peak heights of each component and converted into a measure of micromoles of ethylene produced per hour per culture using conversions derived in a known manner from the standard gas laws. A control flask having no algal cells was run as a part of each experiment as a check for equipment error and gas contamination.

Enzyme activity expressed as micromoles of acetylene reduced per hour was directly proportional to the amount of nitrogenase present and, therefor, to actual nitrogen fixation activity. In order to normalize nitrogen fixation rates for the inevitable variations in the number of cells in replicate cultures, the cells were harvested after the acetylene reduction measurements and the chlorophyll content of each culture was determined as described above. The enzyme activity value just described then was divided by the total chlorophyll content to give a normalized nitrogen fixation rate expressed as micromoles of acetylene reduced per hour per microgram of chlorophyll.

It should be noted that all quantitative measurements reported herein are averages of replicate samples, unless indicated otherwise. In order to insure that the results from replicate samples were comparable in each experiment, each culture flask or plate (Petri dish) was inoculated with approximately the same number of cells as determined by the absorbance of the inoculum at 680 nanometers using the Beckman DU-6 spectrophotomer described above. The absorbance of a suspension of whole cells is proportional to the number of cells present and is a rapid method for estimating cell numbers. In all growth experiments, initial chlorophyll determinations were done at the start of the experiment to confirm that the inocula were uniform. Unless stated otherwise, the inoculum contained a number of algal cells equivalent to 10 micrograms of chlorophyll.

The supports employed in the experimental studies are described in the paragraphs below; except for supports 3, 4, 25, and 26, each support was washed twice with deionized water prior to use.

Support 1

Meltblown polypropylene nonwoven webs having a nominal basis weight of approximately 34 g/m$^2$, with actual basis weights probably varying from about 24 to about 38 g/m$^2$. Support samples were taken from webs having targeted basis weights of 24, 34, and 38 g/m$^2$. No attempt was made to actually measure the basis weight of each individual support sample because basis weight was not deemed to be a significant variable in the attachment of the algae to the support and basis weight determinations for nonwoven webs or fabrics typically are made with relatively large samples because of the web thickness or basis weight nonuniformity inherent in most meltblowing processes.

Support 2

Spunbonded polypropylene nonwoven webs having a nominal basis weight of approximately 34 g/m$^2$, with actual basis weights probably varying from about 24 to about 38 g/m$^2$. Support samples were taken from webs having targeted basis weights of 24, 34, and 38 g/m$^2$. No attempt was made to actually measure the basis weight of each individual support sample because basis weight was not deemed to be a significant variable in the attachment of the algae to the support and basis weight determinations for nonwoven webs or fabrics typically are made with relatively large samples because of the web thickness or basis weight nonuniformity inherent in most spunbonding processes.

Support 3

Milkweed fibers, obtained by manually separating the fibers of dried pods from the placenta and seeds.

Support 4

Thermomechanical wood pulp consisting of at least about 95 percent by weight Southern softwood, with the remainder being Southern hardwood, processed conventionally at temperatures of about 132-144 degrees C. The pulp was washed to a neutral pH before use.

Support 5

A surface-modified meltblown polypropylene nonwoven web having a perfluoromethylated surface. An approximately 10-cm square sample of a meltblown polypropylene nonwoven web having a basis weight of about 24 g/m$^2$ (i.e., support 1) was RF plasma treated by means of a Branson/IPC Model S3000 Plasma System (Branson International Plasma Corporation, Hayward, Calif.). The sample was treated first for five minutes at 30 watts in an argon atmosphere at a pressure of 0.2 Torr, followed by a five-minute treatment at 10 watts in an atmosphere of hexafluoroethane at a pressure of 0.05 Torr.

Support 6

A surface-modified meltblown polypropylene nonwoven web having a perfluoromethylated surface. The support was prepared essentially as described for support 5, except that the first treatment was carried out at 15 watts and the second treatment was carried out for 15 minutes at 20 watts and a pressure of 0.1 Torr.

Support 7

A surface-modified meltblown polypropylene nonwoven web having a perfluoromethylated surface. The support was prepared essentially as described for support 6, except that the second treatment was carried out for five minutes at 5 watts and a pressure of 0.05 Torr.

Support 8

A surface-modified meltblown polypropylene nonwoven web having a pentadecafluorooctyl methacrylated surface. An approximately 10-cm square sample of a meltblown polypropylene nonwoven web having a basis weight of about 24 g/m$^2$ (i.e., support 1) was soaked for five minutes in a solution consisting of 10 percent by weight pentadecafluorooctyl methacrylate and 90 percent by weight methylene chloride. The solvent then was allowed to evaporate. The sample was exposed to an electron beam, using an Electrocurtain TM Model CB 200-45-50-7503 Electron Beam Processor (Energy Sciences, Inc., Woburn, Mass.). The sample was passed through the Processor twice, turned over in order to expose the other side, and passed through two additional times. For each pass, the oxygen level in the processing chamber or reaction zone was less than 500 ppm, the beam current was 4 milliamps, the accelerating voltage was 200 kV, and the line speed was 20 feet per minute. The total radiation dose per side of sample was 8 megarads. The sample then was washed sequentially with methylene chloride and Freon TM 113 and allowed to dry at ambient temperature for eight hours in a fume hood.

Support 9

A commercially available white woven cotton fabric.

Support 10

A commercially available white Pellon ™ nonwoven interlacing, probably of the fusible type, consisting of 70 percent by weight polyester and 30 percent by weight rayon.

Support 11

A commercially available white Pellon ™ nonwoven interlacing, probably of the fusible type, consisting of 50 percent by weight polyester and 50 percent by weight nylon.

Support 12

A commercially available white Pellon ™ nonwoven interlacing, probably of the fusible type, consisting of 70 percent by weight rayon and 30 percent by weight nylon.

Support 13

A commercially available white nylon Pellon ™ nonwoven interlacing, probably of the fusible type.

Support 14

A commercially available white polyester Pellon ™ non-woven interlacing, probably of the fusible type.

Support 15

A meltblown polypropylene nonwoven web having a basis weight of about 38 g/m$^2$ (i.e., support 1). Although identical with support 1, the material was included with the following three supports as a control and therefore required a separate support number.

Support 16

A surface-modified meltblown polypropylene nonwoven web having a perfluoromethylated surface. The support was prepared essentially as described for support 5, except that the second treatment was carried out for 15 minutes at 30 watts and a pressure of 0.2 Torr.

Support 17

A surface-modified meltblown polypropylene nonwoven web having a chlorinated surface. An approximately 10-cm square sample of a meltblown polypropylene nonwoven web having a basis weight of about 38 g/m$^2$ (i.e., support 1) was placed in a Pyrex ® vessel. The vessel was repeatedly evacuated and charged with nitrogen ten times. The vessel then was evacuated to a pressure of 10 mm Hg, charged with chlorine to a pressure of 30 mm Hg, and sealed. Two commercially available sunlamps were located just outside of the vessel, one lamp facing each side of the sample. The sample was illuminated by the sunlamps for five minutes at ambient temperature. The vessel then was flushed with nitrogen five times. The sample was removed from the vessel, rinsed ten times with water, and dried.

Support 18

A surface-modified meltblown polypropylene nonwoven web having a 2-hydroxyethyl methacrylated surface. An approximately 10-cm square sample of a meltblown polypropylene nonwoven web having a basis weight of about 24 g/m$^2$ (i.e., support 1) was dipped in a solution consisting of 80 percent by weight 2-hydroxyethyl methacrylate and 20 percent by weight hexanol. The sample was exposed to an electron beam, essentially as described for support 8. For each pass, the oxygen level in the processing chamber or reaction zone was less than 500 ppm, the beam current was 5 milliamps, the accelerating voltage was 200 kV, and the line speed was 20 feet per minute. The total radiation dose per side of sample was 10 megarads. The sample then was washed ten times with hot water and allowed to dry.

Support 19

A coformed nonwoven web composed of primary fibers of meltblown polypropylene and secondary fibers of debonded chemical wood pulp. The primary fibers constituted 20 percent by weight of the web and the secondary fibers constituted 80 percent by weight of the web. The debonded chemical wood pulp was derived from approximately 80 percent by weight Southern softwood and 20 percent by weight Southern hardwood by the standard sulfate process, followed by a standard five-stage bleaching process (i.e., chlorination, caustic extraction, chlorine dioxide treatment, caustic extraction, and chlorine dioxide treatment).

Support 20

A coformed nonwoven web similar to support 19, except that the web was composed of 35 percent by weight primary fibers and 65 percent by weight secondary fibers.

Support 21

A coformed nonwoven web similar to support 19, except that the web was composed of 50 percent by weight primary fibers and 50 percent by weight secondary fibers.

Support 22

A fibrous, porous form of poly(tetrafluoroethylene), namely, Zitex ® filter membranes, 47 mm in diameter, type 47-C, coarse porosity (Norton Chemplast, Wayne, N.J.).

Support 23

A fibrous, porous form of poly(tetrafluoroethylene), namely, Zitex ® filter membranes, 47 mm in diameter, type 47-F, fine porosity (Norton Chemplast, Wayne, N.J.).

Support 24

Whatman GF/A glass microfiber filters, 5.5 cm in diameter and 0.26 mm thick (Whatman, Inc., Fisher Catalog No. 09-874-16, Fisher Scientific, Pittsburgh, Penna.).

Support 25

Pine sawdust from freshly sawed wood.

Support 26

Debonded chemical wood pulp, derived from approximately percent by weight Southern softwood and 20 percent by weight Southern hardwood by the standard sulfate process, followed by a standard five-stage bleaching process (i.e., chlorination, caustic extraction, chlorine dioxide treatment, caustic extraction, and chlorine dioxide treatment). This was the same type of pulp employed as the secondary fibers in supports 19–21, inclusive.

Support 27

A commercially available white Pellon ™ nonwoven interlacing consisting of 50 percent by weight polyester and 50 percent by weight nylon.

Support 28 A commercially available white Pellon ™ nonwoven interlacing, probably of the fusible type, consisting of 70 percent by weight polyester and 30 percent by weight rayon.

Support 29

A commercially available white Pellon ™ nonwoven interlacing, probably of the fusible type, consisting of 70 percent by weight rayon and 30 percent by weight nylon.

Support 30

A commercially available white polyester Pellon ™ non-woven interlacing, probably of the fusible type.

Support 31

A commercially available white woven cotton fabric.

Support 32

A commercially available white Pellon ™ nonwoven interlacing of the fusible type, consisting of 50 percent by weight polyester and =percent by weight nylon and having a heavy coating on one side.

Support 33

A commercially available white Pellon ™ nonwoven interlacing consisting of 60 percent by weight polyester and 40 percent by weight rayon. The material was verified to be other than the fusible type.

Support 34

A commercially available white polyester Pellon ™ non-woven interlacing. The material was verified to be other than the fusible type.

Support 35

A commercially available white Pellon ™ nonwoven interlacing consisting of 50 percent by weight rayon and 50 percent by weight acetate. The material was verified to be other than the fusible type.

Support 36

A commercially available white Pellon ™ nonwoven interlacing consisting of 70 percent by weight rayon and 30 percent by weight nylon. The material was verified to be other than the fusible type.

Support 37

Wheat straw fragments. The fragments were obtained by processing a mixture of wheat straw and water in a Model 31BL92 Waring Commercial Blendor (Waring Products Division, Dynamics Corporation of America, New Hartford, Conn.) until the straw fragments were no longer than about one inch (about 2.5 cm). The fragments were placed in a large volume of water at a temperature of about 45 degrees C., agitated, then filtered through a fine screen to separate the straw fragments from fines, dirt, and other extraneous matter. This washing procedure was repeated two more times. The straw fragments then were dried in an oven at 100 degrees C. for three hours.

Support 38

A commercially available white nonwoven fabric, James River Cerex ™ 100 percent nylon 6.

Support 39

A meltblown nonwoven web having a basis weight of 34–68 g/m$^2$, meltblown without processing aids from a commercially available poly(butylene terephthalate) resin (Resin No. PBT B-566, Celanese Engineering Resins, Summit, N.J.).

Support 40

A meltblown nonwoven web having a basis weight of 34–68 g/m$^2$, meltblown without processing aids from a commercially available ethylene-vinyl acetate copolymer consisting of 72 percent by weight ethylene and 28 percent by weight vinyl acetate (Resin No. 077-004, Exxon Chemical Company, Baytown, Tex.).

Support 41

A meltblown nonwoven web having a basis weight of 34–68 g/m$^2$, meltblown without processing aids from a commercially available "PET Glycol" copolyester of unknown composition (Eastman Chemical Products, Kingsport, Tenn.).

Support 42

A meltblown nonwoven web having a basis weight of 34–68 g/m$^2$, meltblown without processing aids from a commercially available ethylene-acrylic acid copolymer consisting of 90 percent by weight ethylene and 10 percent by weight acrylic acid (Resin No. 077-4090, Exxon Chemical Company, Baytown, Tex.).

Support 43

A meltblown nonwoven web having a basis weight of 34–68 g/m$^2$, meltblown without processing aids from a commercially available ethylene-methyl acrylate copolymer consisting of 80 percent by weight ethylene and 20 percent by weight methyl acrylate (Resin No. XS-13.04, Exxon Chemical Company, Baytown, Tex.).

The approximate surface energies of the above supports are presented in Table 2. Whenever possible, two values are given one for the fiber and one for the web or fabric. The value for the fiber typically is the generally accepted literature value for a film of the material of which the fiber is composed. The surface energy for the web or fabric is either a generally accepted literature value or and estimate determined by means of either Pillar wetting agents (Pillar Corporation, West Alis, Wisconsin) or solvents or solvent mixtures whose surface tensions were either known or had been measured. The procedure employed with the Pillar wetting agents was an adaptation of ASTM Method D 2578-67, modified to allow for smaller sample or fabric sizes. The wetting agents were applied as drops to a sample. The drops then were removed from the surface of the sample by a blotter. The surface energy of the sample was taken to be the surface tension of the first wetting agent which left a residual blue color in the sample after the blotting process.

TABLE 2

| Summary of Support Surface Energies | | |
|---|---|---|
| Support No. | Fiber Surface Energy[a] | Web or Fabric Surface Energy[a] |
| 1 | 30 | 38 |

TABLE 2-continued
Summary of Support Surface Energies

| Support No. | Fiber Surface Energy[a] | Web or Fabric Surface Energy[a] |
|---|---|---|
| 2 | 30 | 38 |
| 3 | 30 | 30 |
| 4 | 40 | 40 |
| 5 | ND[b] | <22 |
| 6 | ND | <22 |
| 7 | ND | <22 |
| 8 | ND | 48 |
| 9 | >55 | >73 |
| 10 | >50 | >73 |
| 11 | >55 | >73 |
| 12 | 52 | >73 |
| 13 | 41 | >73 |
| 14 | 43 | >73 |
| 15 | 30 | 38 |
| 16 | ND | <22 |
| 17 | ND | 50 |
| 18 | ND | 72 |
| 19 | 30–40 | ≈60 |
| 20 | 30–40 | ≈60 |
| 21 | 30–40 | ≈60 |
| 22 | 19 | ND |
| 23 | 19 | ND |
| 24 | 120 | 120 |
| 25 | ≈35 | NA[c] |
| 26 | 40 | NA |
| 27 | >55 | >73 |
| 28 | >50 | >73 |
| 29 | 52 | >73 |
| 30 | 43 | >73 |
| 31 | >55 | >73 |
| 32 | >55 | >73 |
| 33 | >50 | >73 |
| 34 | 43 | >73 |
| 35 | 46 | >73 |
| 36 | 52 | >73 |
| 37 | 29 | NA |
| 38 | 45 | >73 |
| 39 | 37 | 59 |
| 40 | 33 | 50 |
| 41 | 49 | >73 |
| 42 | 48 | >73 |
| 43 | 31 | 39 |

[a]Estimated value in dynes per cm.
[b]Not determined.
[c]Not applicable.

It must be emphasized that each of the values reported in Table 2 is only an approximation. It is known that the apparent surface energy of a porous material often is higher than the surface energy of the same material in the form of a film. Stated differently, the contact angle of a drop of liquid of a surface can be reduced substantially as a result of surface roughness (or porosity) and/or capillary effects. This phenomenon leads to an apparent surface energy for a porous surface which is higher than the surface energy which would be measured on a smooth film of the material of which the porous surface is made.

While each algal cell or filament probably "sees" only individual fibers, it exists in an aqueous environment. Consequently, the apparent surface energy of the support has to have an effect on the attachment of a cell to a support fiber. It also is likely that the actual surface energy of the fiber has an effect on cell attachment. The extent of these effects, however, remains unknown, especially in view of the fact that a number of the supports are bicomponent materials having, at least in a few instances, different surface energies.

For the foregoing reasons, the use of surface energies herein must not be construed too narrowly. Nevertheless, surface energy provides a useful and convenient means for defining the present invention.

The initial or first phase experiments were aimed at determining whether or not (1) the filamentous heterocystous blue-green algae would grow and fix nitrogen in the presence of the above natural and synthetic supports and (2) the algal cells would attach to the supports. These experiments also were intended to serve as preliminary tests of experimental designs for the quantitative determinations of growth and nitrogen fixation rates.

The supports studied in these initial experiments were supports 1–4, inclusive, described above. Samples of each support were sterilized and placed in level 1 culture flasks containing the specified volume of medium. Each flask then was inoculated with a small number of algal cells. The cells were allowed to grow for one week, after which time the flasks were examined visually. Replicate experiments were run in all cases and medium with and without nitrogen was employed with each support.

After growth for one week, it was evident that the blue-green algae were able to grow well in the presence of all of the supports tested, whether or not nitrogen was present in the medium. The normal growth observed in the nitrogen-free medium indicated that the algae were able to carry out nitrogen fixation unhindered by the presence of support. Significantly, the algal cells attached to all of the supports only when the medium did not contain nitrogen; i.e., only when the algae were fixing nitrogen (this attachment phenomenon will be discussed in greater detail later). Moreover, the attached algae appeared to grow and fix nitrogen.

The second phase of experiments was directed primarily at determining (1) the growth rates of the attached or immobilized cells; (2) the affinity of the algal cells for the various supports, i.e., the extent of attachment of the cells to the supports; and (3) the effect of attachment or immobilization on the nitrogen-fixation rates of the algal cells.

Initially, these experiments were carried out with cells in liquid culture. It was necessary to use liquid cultures to measure cell attachment since it was not possible to distinguish between attachment and a passive association among cells grown on solid media. That is, cells can rest on a surface without actually attaching to the surface; such a passive association between algal cells and a solid substrate is, in fact, not an uncommon occurance in nature. In a liquid culture, however, passively associated cells are readily washed from the surface of the support. Thus, any cells remaining on the support after a washing procedure has been carried out must represent attached or immobilized cells. In this regard, it perhaps should be emphasized that the term "immobilized", as used herein, means nothing more than an attachment of the algal cells to a support by any mechanism. In addition, during the early stages of these second phase experiments, techniques for measuring growth and nitrogen-fixation rates had not been adapted for use with cultures grown on solid media.

All second phase experiments were carried out with cells grown in nitrogen-free media so that any growth observed was supported by nitrogen fixation. Moreover, as already noted, immobilization occurred only when the cells were fixing nitrogen, i.e., when the cells were grown in nitrogen-free media. As with the first phase experiments, all results represent the average of several replicate samples, unless indicated otherwise. It perhaps should be noted that not all of these second phase experiments were run at the same time. A number of supports were examined later, after insight into the method of attachment of the algal cells to the supports had been acquired.

To determine the ability of the algal cells to grow in the presence of a support, cells were cultured in the presence and absence of the support. At the end of the incubation period, total chlorophyll determinations were carried out on both cultures. The growth of algal cells in the presence of the support was defined as the ratio of the total number of cells obtained in the presence of the support to the number of cells obtained in the absence of the support, expressed as a percentage.

The growth studies were conducted in two separate but similar sets of experiments. In the first set of experiments involving supports 1-4, inclusive, a sufficient number of replicates were run so that total chlorophyll determinations could be run at the beginning of the incubation period (time zero), after an incubation time of three days, and at the end of the one week incubation period. Each sample of support was added to a level 1 culture flask containing 50 ml of nitrogen-free medium. The flasks were inoculated with an equal number of algal cells and incubated as already described. Total chlorophyll determinations were run at the indicated time intervals. The data thus obtained were plotted, which plot is shown as FIG. 1.

From FIG. 1, it is seen that the growth behavior of the algae immobilized on or attached to the various supports studied did not vary significantly from that of algae growing in liquid culture in the absence of a support, with the possible exception of support 4, thermomechanical wood pulp. In the presence of support 4, the algae apparently grew normally for the first three days and then underwent a slight reduction in the growth rate by the end of the one week period. As will be made evident later, however, support 4 is an especially good support for the growth and attachment of algal cells. While the results shown by FIG. 1 with respect to support 4 may be an artifact, a suspension of the support in medium was cloudy, thereby limiting the amount of light reaching algae in portions of the culture vessel other than adjacent to the vessel wall. It is likely that the reduced growth rate seen for support 4 was the result of this light-limiting phenomenon. The growth data for the four supports at the end of the one week incubation period are presented in Table 3, expressed as a percentage of the growth observed in the control culture.

TABLE 3

| Growth Studies with Various Supports in Liquid Culture | |
|---|---|
| Support | Percent Growth[a] |
| Control | 100 |
| 1 | 101 |
| 2 | 112 |
| 3 | 118 |
| 4 | 40 |

[a]Growth as a percent of the control.

In the second set of experiments, total chlorophyll determinations were run only at the end of the incubation period. The second set consisted of two groups of experiments. Although each group included a control culture, they were run at two different times. Consequently, the data for the two groups cannot be compared directly and are reported separately in Tables 4 and 5.

TABLE 4

| Growth Studies with Various Supports in Liquid Culture | |
|---|---|
| Support | Percent Growth[a] |
| Control | 100 |
| 5[b,c] | 108 |
| 6[b,c] | 98 |
| 7[b,c] | 68 |
| 8[b,c] | 95 |

[a]Growth as a percent of the control.
[b]Replicate samples were not employed.
[c]The support was used as received.

TABLE 5

| Growth Studies with Various Supports in Liquid Culture | |
|---|---|
| Support | Percent Growth[a] |
| Control | 100 |
| 9 | 50 |
| 10 | 4 |
| 11 | 4 |
| 12 | 0 |
| 13 | 13 |
| 14 | 2 |

[a]Growth as a percent of the control.

Except for supports 10-14, inclusive, the data in Tables 3-5, inclusive indicate that the cells grow reasonably well in the presence of a support. The very poor growth behavior observed with supports 10-14, inclusive, may be due to the presence on or in the supports of one or more deleterious substances, such as lubricants, sizes, post-treatment chemicals such as mercerizing agents, and the like, which either inhibit growth or actually kill the algal cells. As a result of two later attempts, described infra, to achieve attachment to and growth on commercially available nonwoven fabrics, it became apparent that each of supports 10-14, inclusive, probably was of the fusible type. Fusible interlacing materials are coated with a thermoplastic adhesive which permits the fabric to be attached to another fabric by the application of heat, e.g., by ironing.

The affinity studies were carried out essentially as described for the growth studies. The affinity of the algal cells for a given support, expressed as the percentage of cells present in the culture which were attached to the support, was determined by measuring the number of cells in the culture which were attached to the support and the number of cells remaining in the medium. Each sample of support was added to a level 1 culture flask containing 50 ml of nitrogen-free medium. The flasks were inoculated with equal numbers of algal cells and incubated for one week as already described. At the end of the incubation period, the support was removed from each flask in such a manner as to wash the support with culture medium. The cells remaining in the medium were harvested. The chlorophyll contents of the cells associated with the support and the harvested cells were measured. The total number of cells present in the culture at the end of the incubation period was taken to be the sum of the number of cells associated with the support and the number of cells harvested. The affinity of the algal cells for the support then was calculated as the percentage of the total number of cells present in the culture medium which were attached to the support. The results of the affinity studies are summarized in Table 6.

TABLE 6

Summary of Affinity Studies
with Various Supports in Liquid Culture

| Support | Percent Cells Attached |
|---|---|
| 1 | 88 |
| 2 | 98 |
| 3 | 97 |
| 4 | 88 |
| 5[a] | 64 |
| 6[a] | 51 |
| 7[a] | 47 |
| 8[a] | 77 |
| 9 | 89 |
| 10 | 96* |
| 11 | 99* |
| 12 | 0* |
| 13 | 95* |
| 14 | 63* |
| 15[b] | 40 |
| 16[b] | 25 |
| 17[b] | 34 |
| 18[b] | 95 |
| 19 | 90 |
| 20 | 87 |
| 21 | 97 |
| 22 | 3 |
| 23 | 2 |
| 24 | 87 |
| 26 | >90[c] |

[a]Replicate samples were not employed.
[b]The support was washed twice with distilled water before use.
[c]Based on visual observation only; although the algae attached well, the support with attached algae could not be separated from suspended, nonattached algae since the sizes of the nonattached algae and the support particles were of the same order of magnitude.

Upon examining the data in Table 6, it is evident that the results marked with an asterisk (*) cannot be taken at face value in view of the growth studies summarized in Table 5. Except for support 9, the observed growth behavior for each of supports 10–14, inclusive, relative to that of a culture grown in the absence of any support, was either zero or so low as to be insignificant. For the present at least, it appears that the cells were able to attach to supports 10–14, inclusive, with a concomitant inhibition of growth. In fact, from a visual observation of the culture flasks, some of the cells appeared to be dead. The growth rate observed for support 9 was lower than expected, again perhaps due to the presence of a deleterious substance on or in the support fibers.

Because the results obtained with supports 9–14, inclusive, possibly were caused by one or more toxic materials associated with each support, a second set of similar supports was obtained. Because it could not be determined whether or not any support of this second set was identical with one of supports 9–14, inclusive, the supports in this second set were given support numbers 27–32, inclusive. Each support initially was an approximately 6×14 inch (approximately 15×36 cm) piece of material.

Before carrying out affinity studies with supports 27–32, inclusive, the supports as a group were agitated sequentially with about 2 liters of (1) hexane at ambient temperature for one hour, (2) 200 proof ethanol at ambient temperature for one hour, (3) the same 200 proof ethanol at reflux temperature for one hour, and (4) water at ambient temperature for two hours. The supports were air dried in a fume hood for three hours, and then at a pressure of about 0.5 Torr for one hour.

The affinity studies described for supports 9–14, inclusive, were carried out, using appropriate amounts of each of supports 27–32, inclusive, except that the incubation period was reduced to four days. The results obtained are summarized in Table 7.

татабле 7

Summary of Affinity Studies
with Various Supports in Liquid Culture

| Support | Total Chlorophyll[a] | Percent Cells Attached |
|---|---|---|
| 27 | 44 | 95 |
| 28 | 0[b] | ND[c] |
| 29 | 0[b] | ND[c] |
| 30 | 0[b] | ND[c] |
| 31 | 92 | 95 |
| 32 | 0[b] | ND[c] |

[a]Micrograms chlorophyll per culture.
[b]Below the detection level.
[c]Not determined; initially, cells appeared to attach but soon died, making it impossible to determine the percentage of cells attached to the support.

Although a control culture having no support present was not included, it is evident from the total chlorophyll analyses that growth occurred with supports 27 and 31. As noted earlier, the inoculum for each level 1 flask used in the growth and affinity studies contained a number of cells which was approximately equivalent to 10 micrograms of chlorophyll. After four days, the total chlorophyll in these two cultures had increased approximately four fold and ten fold, respectively. In addition, the attachment level in each case was very high.

It seems probable that support 27 was not of the fusible type and that neither support 27 nor support 31 contained materials which were significantly toxic to the algae. It is possible, however, that support 27 was of the fusible type, but that the coating material was more readily removed from the material. This possibility, though, is believed to be unlikely. Interestingly, the remaining four supports appeared to be more toxic to the algae than supports 10–14, inclusive. Perhaps the solvent extraction procedures employed with supports 27–32, inclusive, rendered some deleterious substance(s) more soluble or more available to the algae. If residual solvents were present in supports 27–32, they apparently had little, if any, detrimental effect on the algae since supports 27 and 31 supported the growth of algae. However, the reason for the approximately two fold greater growth with support 31 as compared to support 27 is not known.

In an effort to understand the results obtained with the interlacing materials examined thus far, supports 33–36, inclusive, were obtained. During the procurement process, however, the existence of two types of interlacing was discovered. This time all supports were verified as being of the nonfusible type.

Because the supports still could have processing aids or other chemicals present in or on the material, the supports were treated as a group by the following procedure: the supports were washed once in a standard home washing machine, using only three drops of dish detergent. The supports then were subjected to three rinse cycles. After drying, the supports as a group were agitated sequentially with about 2 liters of (1) hexane at ambient temperature for one hour, (2) 200 proof ethanol at ambient temperature for one hour, and (3) water at ambient temperature for about ten minutes. The supports then were air dried in a fume hood.

Because the autoclaving procedure could bring additional deleterious substances to the surfaces of the fibers, even if the washing and extraction procedure were effective, autoclaving was replaced with a washing with 70 percent ethanol, followed by air drying.

The affinity studies already described were repeated with supports 33-37, inclusive. Once again the incubation period was reduced to four days. This time, however, control cultures were included. The results obtained are summarized in Table 8.

TABLE 8

Summary of Affinity Studies with Various Supports in Liquid Culture

| Support | Relative Growth | Percent Cells Attached |
|---|---|---|
| Control | 100 | NA[a] |
| 33 | 49 | 95 |
| 34 | 69 | 98 |
| 35 | 6 | 98 |
| 36 | 39 | 86 |

[a]Not applicable.

In every case, algae attached well to the support but growth appeared to be inhibited relative to the control, especially with support 35. These results suggest that the washing and extraction procedure was effective in removing deleterious substances from the surfaces of the fibers, but that additional substances remained within the fibers. During the incubation period, these additional substances slowly migrated to the fiber surfaces, thereby inhibiting growth. The autoclaving process is believed to have caused a rapid migration of such substances, resulting in substantially higher concentrations which killed the algal cells. Although these results are not unequivocal, it is apparent that the fabric type supports studied are not inherently poor supports. That is, the experimental results are not the result of inherently adverse characteristics associated with the materials from which the fibers are made.

In an effort to minimize or eliminate the presence of possibly deleterious substances from fabric-type supports, the affinity studies were repeated with supports 38-43, inclusive. All of the supports were sterilized with 70 percent alcohol. Autoclaving, however, could be carried out only with supports 38 and 39; all of the other supports melted or fused. The results are summarized in Table 9; for completeness, the results from both sterilization methods are reported where applicable. Although a control was included, i.e., a culture of algal cells in suspension without any support material present, it is not included in the table because of the format used. As with the preceeding studies, relative growth is simply the growth observed with a given support relative to the growth obtained with the control; that is, the control represented 100 percent growth.

TABLE 9

Summary of Affinity Studies with Various Supports in Liquid Culture

| Support | Relative Growth EtOH | Relative Growth Heat | Percent Cells Attached EtOH | Percent Cells Attached Heat |
|---|---|---|---|---|
| 38 | 44 | 44 | 88 | 84 |
| 39 | 49 | 50 | 92 | 98 |
| 40 | 51 | NA[a] | 10 | NA |
| 41 | 59 | NA | 52 | NA |
| 42 | 71 | NA | 96 | NA |
| 43 | 56 | NA | 98 | NA |

[a]Not applicable.

Growth with this group of fabrics or webs generally was better than that observed with any of the preceding groups. However, the results obtained are qualitative only, since many growth variables were not controlled. For example, all of the fabrics floated on the surface of the culture medium. This could have limited access of algal cells to the support, reduced the amount of light available to the algae, or in some other manner caused a reduction in growth relative to the control. Significantly, the algae in every case remained viable. Except for supports 40 and 41, high levels of attachment of algal cells were observed. However, cells did attach to supports 40 and 41, albeit at lower levels. Not unexpectedly, the method of sterilization does not appear to play a role in either growth or attachment.

It should be noted at this point that attempts to attach the algae to support 37 were unsuccessful. Autoclaving the support apparently caused either degradation to give, or solubilization of, components having toxicity to the algae.

Having established that blue-green algae grow in the presence of and attach to a wide variety of supports if such supports are substantially free of substances having a significant deleterious effect on the viability of the algae, initial experiments were conducted to determine the effect of attachment on the nitrogen-fixing capability of the algae. As with the growth and affinity studies, a sample of support was added to a level 1 culture flask containing 50 ml of nitrogen-free medium. Each flask was inoculated with an equal number of algal cells and incubated for one week as already described. Replicates were run for each support, and replicate control cultures lacking a support were included. At the end of the incubation period, the nitrogen-fixing activity of each culture was measured by means of the acetylene reduction technique described hereinbefore. The results of this initial study are summarized in Table 10.

TABLE 10

Nitrogen-Fixing Activity in Liquid Cultures of Algae Immobilized on Various Supports

| Support | Activity[a] | Relative Activity |
|---|---|---|
| Control | 2.14 | 1.00 |
| 1 | 7.44 | 3.48 |
| 2 | 7.02 | 3.28 |
| 3 | 4.05 | 1.89 |
| 4 | 7.51 | 3.51 |

[a]The average of replicate runs for each support, expressed as micromoles of acetylene reduced per hour per microgram of chlorophyll, times $10^3$.

In each case, the immobilized algae showed a nitrogen fixation activity which is significantly higher than that of algae growing suspended in a liquid culture medium. These results were unexpected, especially since the growth characteristics of immobilized algae are essentially the same as those of the nonattached algae; see FIG. 1 and Table 3, supra. Consequently, the data suggest that the immobilized algae are fixing nitrogen at a rate significantly in excess of cellular growth requirements, which excess should be excreted by the cells into the surrounding environment.

As a consequence of the foregoing results, three additional nitrogen fixation studies were carried out with different supports. The results of these studies are summarized in Tables 11-13, inclusive, since the studies were not carried out at the same time.

TABLE 11

Nitrogen-Fixing Activity in Liquid Cultures of Algae Immobilized on Various Supports

| Support | Activity[a] | Relative Activity |
|---|---|---|
| Control | 5.2 | 1.00 |
| 5 | 3.1 | 0.60 |

TABLE 11-continued

Nitrogen-Fixing Activity
in Liquid Cultures
of Algae Immobilized on Various Supports

| Support | Activity[a] | Relative Activity |
|---|---|---|
| 6 | 2.7 | 0.52 |
| 7 | 3.7 | 0.71 |
| 8 | 5.1 | 0.98 |

[a] The average of replicate runs for each support, expressed as micromoles of acetylene reduced per hour per microgram of chlorophyll, times $10^3$.

TABLE 12

Nitrogen-Fixing Activity
in Liquid Cultures
of Algae Immobilized on Various Supports

| Support | Activity[a] |
|---|---|
| 15 | 5.7 |
| 16 | 4.3 |
| 17 | 4.6 |
| 18 | 8.5 |

[a] The average of replicate runs for each support, expressed as micromoles of acetylene reduced per hour per microgram of chlorophyll, times $10^3$.

TABLE 13

Nitrogen-Fixing Activity
in Liquid Cultures
of Algae Immobilized on Various Supports

| Support | Activity[a] |
|---|---|
| 19 | 4.4 |
| 20 | 3.3 |
| 21 | 3.1 |

[a] The average of replicate runs for each support, expressed as micromoles of acetylene reduced per hour per microgram of chlorophyll, times $10^3$.

Because controls were not run at the time the data in Tables 12 and 13 were obtained, relative activities for the supports listed therein could not be calculated. Assuming that the result reported in Table 10 for the control is reasonably representative, the activity levels for the supports listed in Tables 12 and 13 certainly appear to be at least as great as the activity level for nonattached algae. Moreover, the data in Table 12 suggest that the activity levels of the immobilized algae are greater than the activity level for nonattached cells.

The results reported in Table 11 appear to be anomalous when compared with all of the other nitrogen fixation data, at least in the sense that the nitrogen-fixing activities of the algae attached to the supports listed in Table 11 are not greater than the activity of nonattached algae However, the immobilized algae still possess nitrogen-fixing activity.

The experiments with the blue-green algae in liquid media generally involved two subpopulations of cells, those which are attached to a support and those which are not, i.e., those which remain unattached and suspended in the culture medium. Even with those supports having a very high affinity for the algal cells, there always were present at least some cells in the second subpopulation. That is, it was never possible to attach all of the cells to the support. Moreover, the proportion of unattached cells seemed to remain relatively constant. The most probable explanation for this phenomenon is that, as the attached filaments of algal cells grow in a liquid culture, some of the filaments break as a result of fluid turbulence, i.e., the constant agitation or shaking of the culture medium. Such breakage releases filament fragments into the culture medium. Even though such fragments should be capable of subsequent attachment to the support, an equilibrium between breakage and subsequent attachment eventually would be established, thereby accounting for an essentially constant proportion of unattached cells in the medium. That this actually is the case was demonstrated by the experiment which follows.

A series of 12 level 1 flasks containing approximately 0.05 g of polypropylene fibers, i.e., support 1, were inoculated with approximately equal numbers of cells, i.e., the number of cells equivalent to 10 micrograms of chlorophyll. The flasks were divided into four groups of three flasks each, which groups are referred to herein by the letter designations A-D, inclusive. The resulting cultures were incubated for two hours, after which time the group A cultures were analyzed to determine the proportion of cells attached to the support. According to the data (not included), an average of 91 percent of the total cell population was attached to the polypropylene fibers. The remaining nine flasks were incubated for six days, after which time the group B cultures were analyzed as before. This time, an average of 99 percent of the total cell population was attached.

The support with attached cells was carefully removed from the culture medium in each of the flasks of group C and placed in three new flasks containing fresh, cell-free medium; these new cultures will be referred to as group E. To the supernatant medium of each of the group C flasks was added approximately 0.05 g of new support, i.e., polypropylene fibers; these flasks became group F. The group D, E, and F cultures then were incubated an additional six days. At the end of the incubation period, all flasks were analyzed for the percent of the total cell population attached to the support. The average attachments for the three groups were 99, 97, and 99 percent, respectively. The average total growth in the group D cultures was 120 times the number of cells in the inoculum. The combined average total growth in the group E and F cultures also was 120 times the number of cells in the inoculum. These results are illustrated graphically as follows:

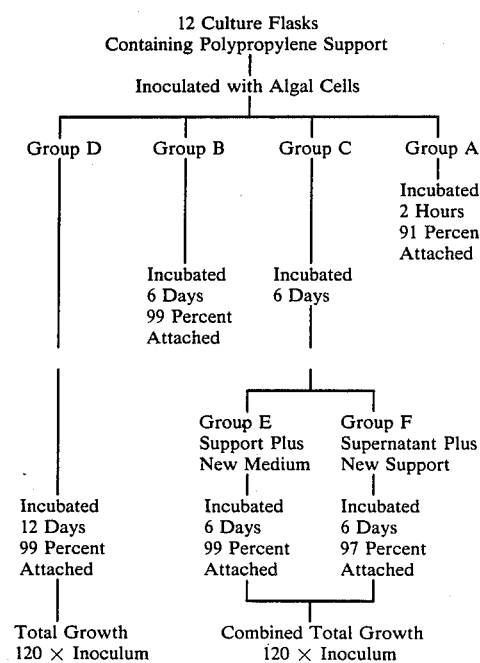

Interestingly, the total growth and the percent of cells attached to the support was essentially the same for the group C and D cultures, even though the group C cultures were treated differently. The results demonstrate that immobilized or attached cells are able to grow; that is, cell growth was not limited to only the unattached population. Furthermore, the unattached cells were able to attach to support and grow. Thus, there appears to be normal breakage of filaments during growth and the filaments clearly are capable of reattaching through either existing or newly formed heterocysts and subsequently continue to grow. It is probable that support surface area plays a major role in determining the growth characteristics of the cells, particularly with respect to the maximum loading of cells per unit mass of support, but this factor was not explored experimentally.

In the very first experiments using support 4, the wood pulp fibers were used as received. Not only did no growth take place, but the cells also died in the presence of the support. Consequently, the fibers were washed with distilled water to a neutral pH which contributed to the very favorable and unexpected results reported thus far with this and the other supports.

Because the wood pulp fibers had been processed thermomechanically, there was an interest in determining whether or not unprocessed wood fibers were capable of permitting the attachment of the algal cells to the wood fibers, or at least allowing the algal cells to grow in a normal manner. To this end, growth studies were carried out with cultures in the presence and absence of unprocessed wood fibers. The wood fibers consisted of clean sawdust from freshly sawed yellow pine, i.e., support 25. All culture flasks were innoculated with a number of algal cells which was equivalent to approximately 10 micrograms of chlorophyll and the support, when present, was added at a level of about 0.05 g per flask, in accordance with the standard procedures established herein for such studies. After being incubated for three days, the chlorophyll content of the cultures lacking support (the control cultures had increased on the average by a factor of five. On the other hand, the chlorophyll content of the cultures containing support had decreased on the average by a factor of ten. After one week, the control cultures showed an approximately 600-fold average increase in total chlorophyll, but no chlorophyll was detected in the cultures containing support. From the foregoing, it is evident that the unprocessed wood fibers and unwashed wood pulp fibers contain one or more substances which are deleterious to the growth and attachment of the algal cells, i.e., the viability of the cells. Accordingly, any support which is used in the present invention must be substantially free of such substances.

All of the experiments described thus far were carried out in liquid cultures. However, a major expected use for the immobilized algae is as a source of nutrients in agriculture. Thus, in order to assess the performance of the immobilized algae under conditions similar to those expected in such use, it was desirable to develop techniques for studying algae grown on solid surfaces.

Agar-solidified medium (ASM) has been used in the past as a surface for the growth of many different types of organisms. Blue-green algae have been grown on agar surfaces for qualitative characterization studies and genetic analysis. However, techniques for measuring algal growth and nitrogen-fixation characteristics apparently have not been developed. In order to fully characterize immobilized algae growing on a solid surface, though, it was Fortunately, such techniques applied primarily to the removal of cells from the agar surface since the analyses could be carried out essentially as described for liquid cultures. Cells grown in the absence of a support were removed from the agar surface by means of one or more cotton-tipped swabs; an effort was made to remove all of the cells. When cells were grown on a support, it often was possible to simply pick up the support with tweezers or a small spatula. Otherwise, the support was carefully scrapped from the ASM surface.

In order to carry out the acetylene reduction assay for estimating the nitrogen-fixing characteristics of the algae grown on a solid surface, the lid of the Petri dish was removed and the dish was placed in a one-pint, wide-mouthed canning jar. The jar was sealed with a rubber stopper through which a section of glass tubing had been inserted. The exterior end of the glass tubing was sealed with a rubber septum. To the jar was added a volume of acetylene sufficient to provide a gaseous mixture in the jar which consisted of 10 percent by volume acetylene. The acetylene reduction assay then was conducted essentially as described earlier, with gas samples being removed via the septum-stoppered glass tubing.

The growth characteristics of immobilized algae grown on a nitrogen-free ASM surface were determined for several supports. The algae first were immobilized on the support by incubating a mixture of the support and a suspension of algal cells in nitrogen-free medium for about two hours, as already described. The resulting algal cell/support composite then was removed from the liquid culture and placed on an ASM surface in a Petri dish. Each dish was covered and incubated for nine days. A sufficient number of replicates was run with each support so that total chlorophyll analyses could be run periodically on several replicates. In addition, control replicates in which the algal cells were placed directly on the ASM surface also were run. The total chlorophyll determinations were carried out at three-day intervals. The data obtained are summarized in Table 14 and plotted as FIG. 2.

TABLE 14

| | Summary of Growth Studies of Algae on Various Supports on Solidified Medium | | | | | |
|---|---|---|---|---|---|---|
| | Micrograms Chlorophyll | | | | 9/0 | Percent |
| Support | 0 Days | 3 Days | 6 Days | 9 Days | Value[a] | Control[b] |
| Control | 1.7 | 8.7 | 41.9 | 93.1 | 55 | 100 |
| 1 | 1.3 | 1.9 | 3.6 | 6.1 | 5 | 10 |
| 3 | 1.6 | 4.6 | 23.8 | 45.9 | 29 | 52 |
| 4 | 2.8 | 16.9 | 137.0 | 298.5 | 107 | 194 |

[a]Normalized growth after 9 days, calculated by dividing the 9 day value by the 0 day value.
[b]Based on normalized growth results after 9 days.

Figure 2:
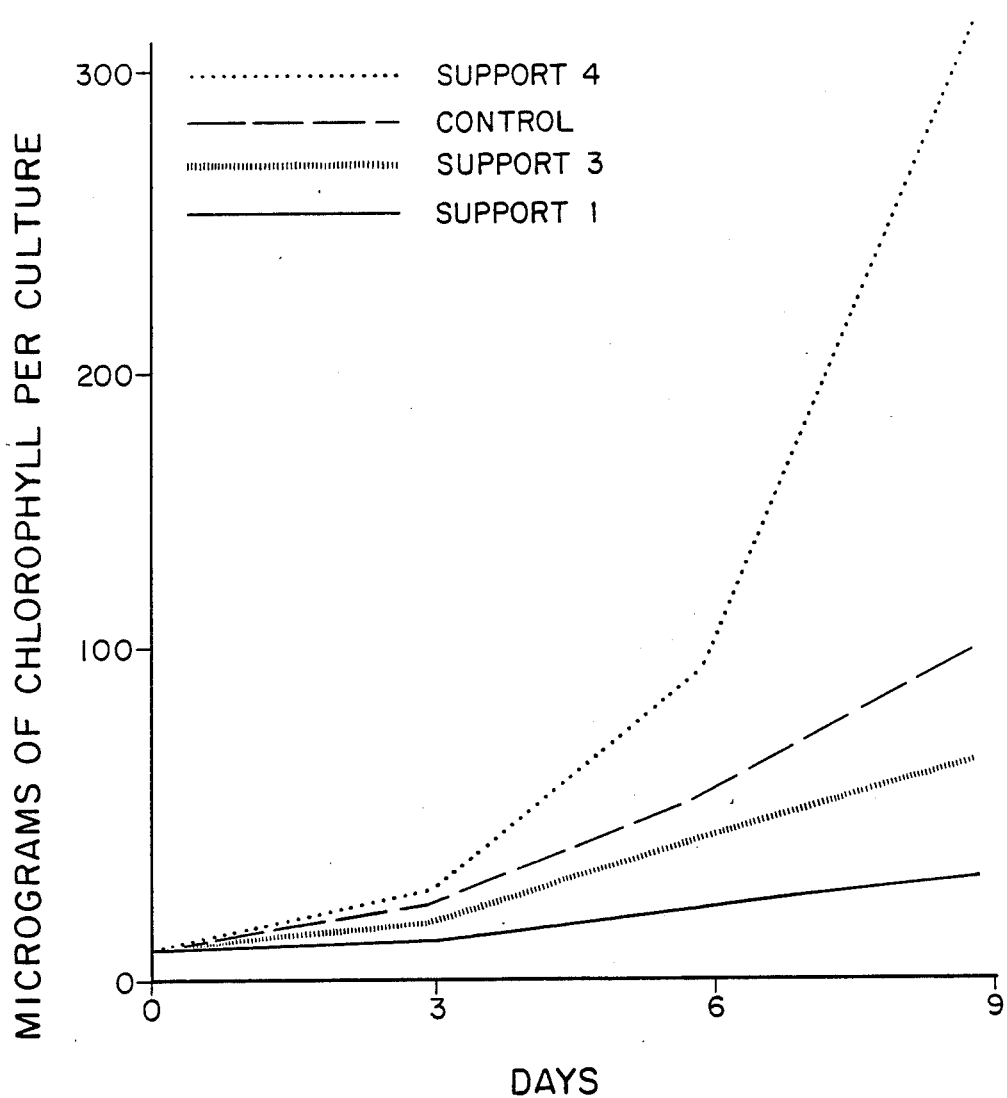
FIG. 2 is a plot of algal growth on each of three different supports and in a control culture, all on agar plates, against time.
Figure 3:
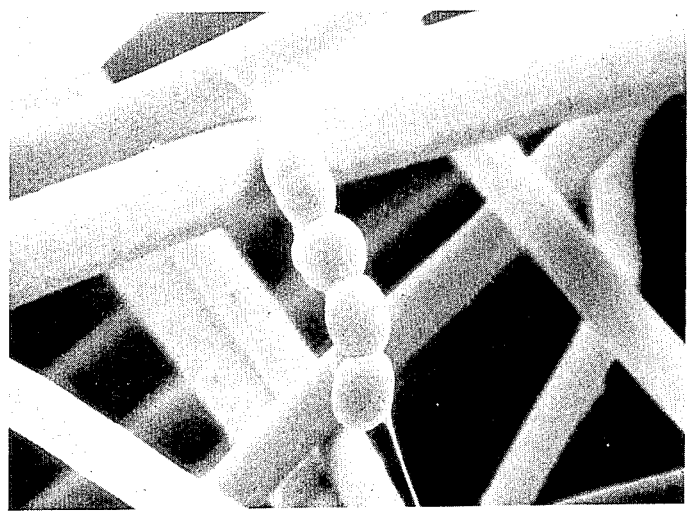
Figure 4:
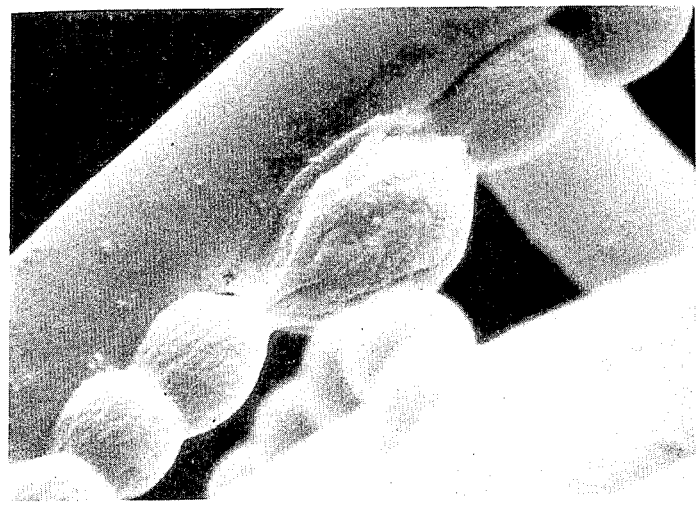
Figure 5:
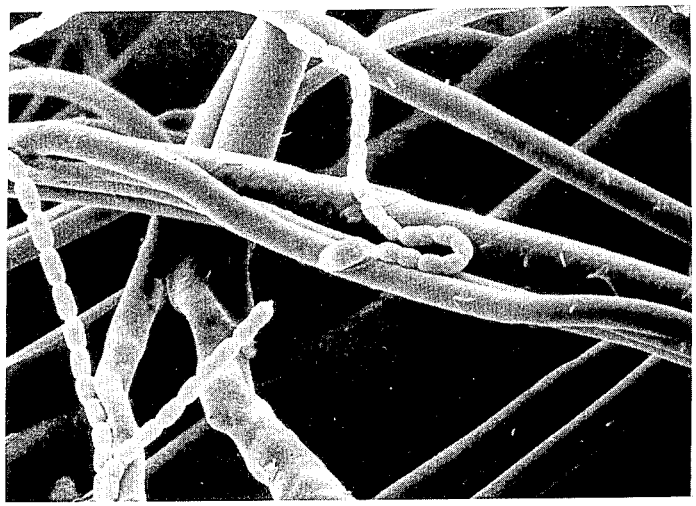
Figure 6:
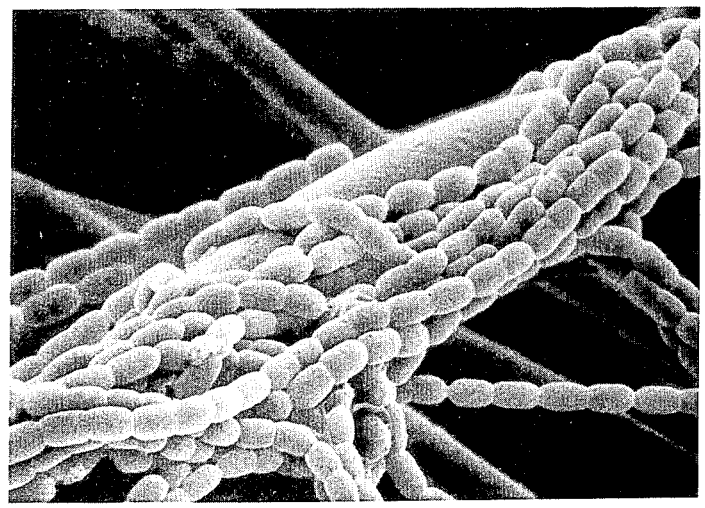
Figure 11:
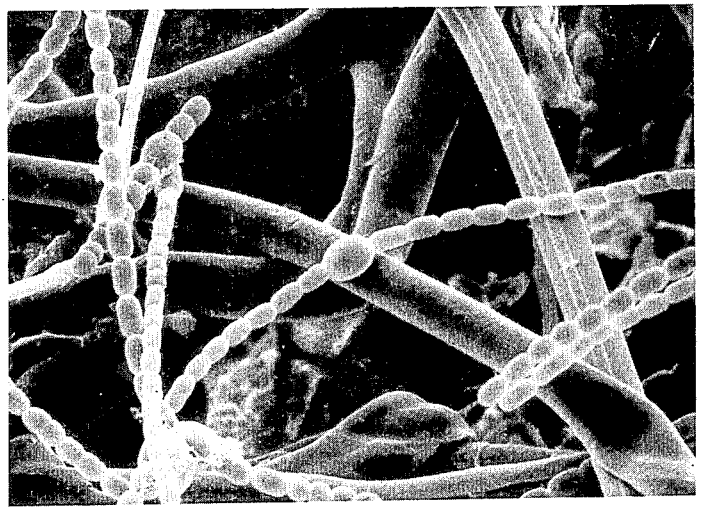
Figure 12:
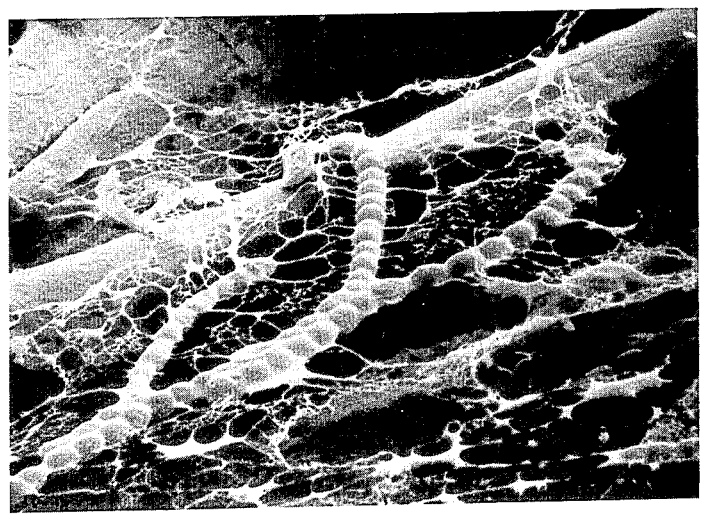
Figure 13:
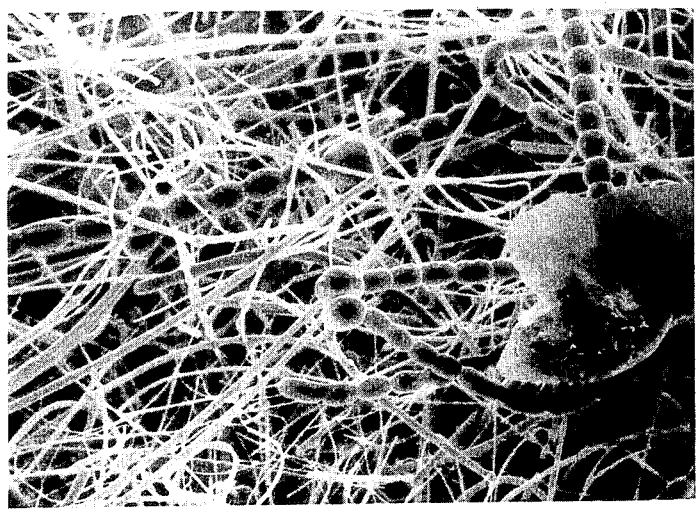
Figure 14:
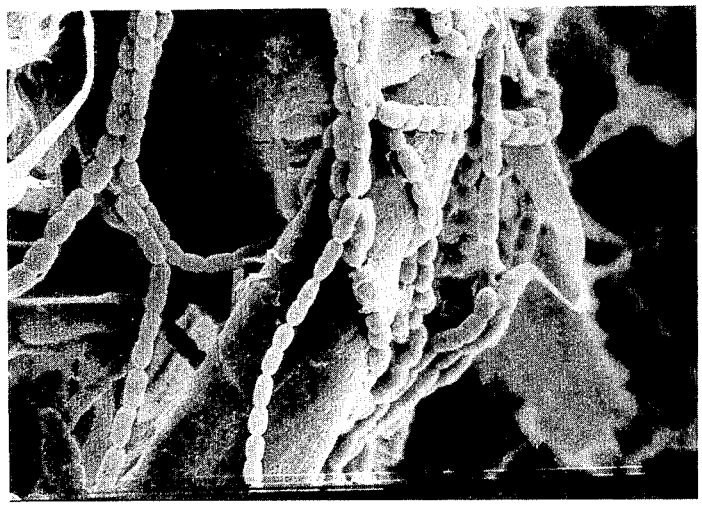
Figure 15B:
Figure 15A:
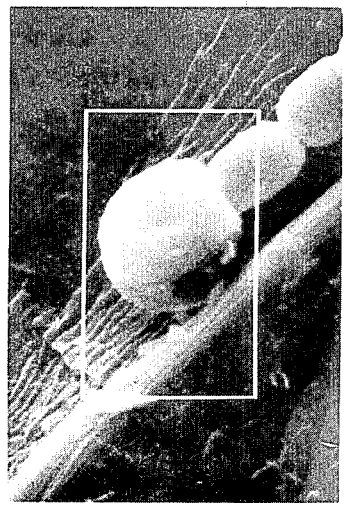
Figure 16:
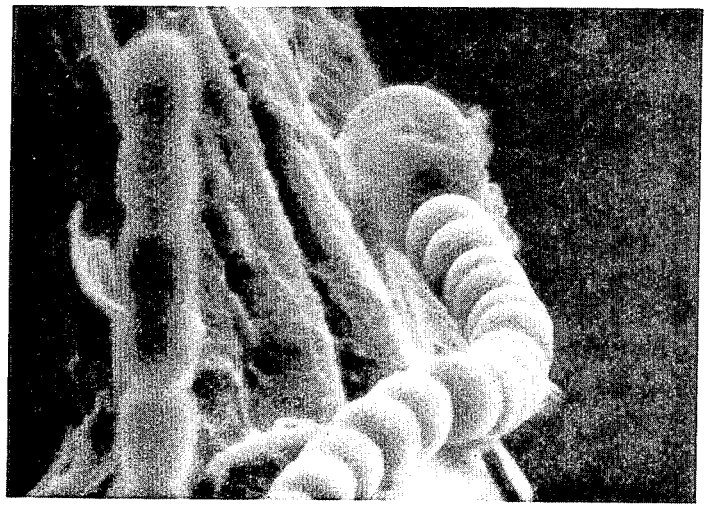
Figure 17:
Figure 18:
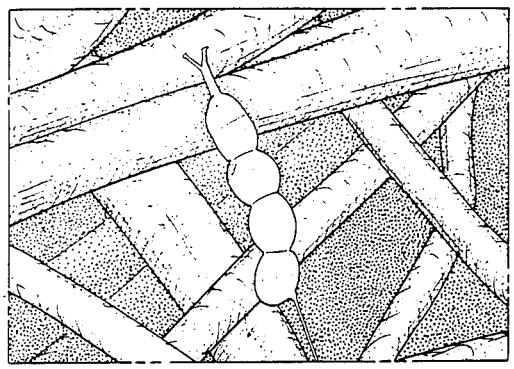
FIGS. 18–32, inclusive, are hand-drawn representations of the actual scanning electron micrographs reproduced as FIGS. 3–17, respectively.
Figure 19:
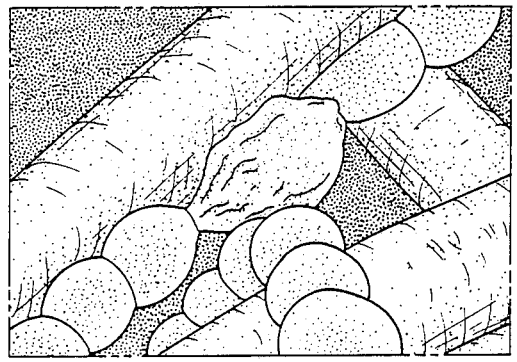
Figure 20:
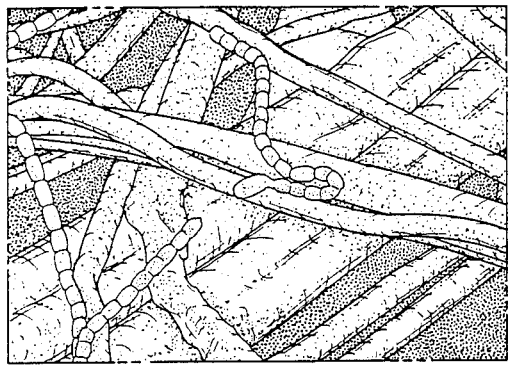
Figure 21:
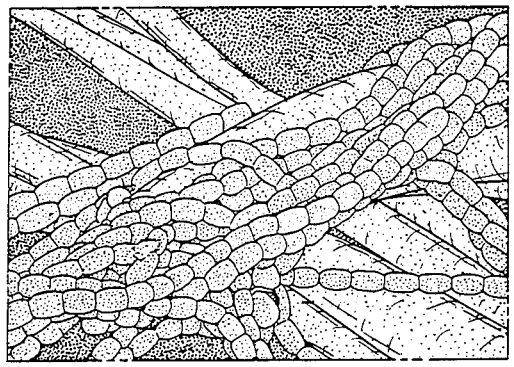
Figures 22A, 22B:
Figure 23:
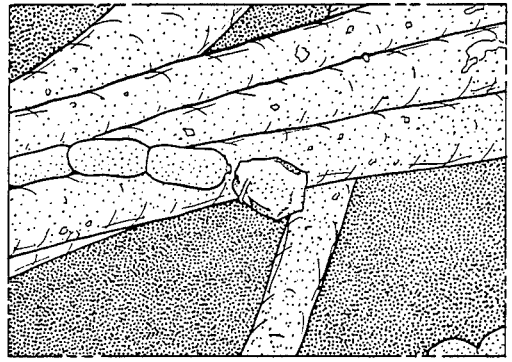
Figures 24A, 24B:
Figure 25:
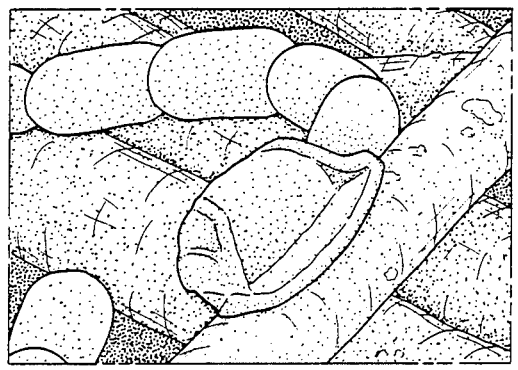
Figure 26:
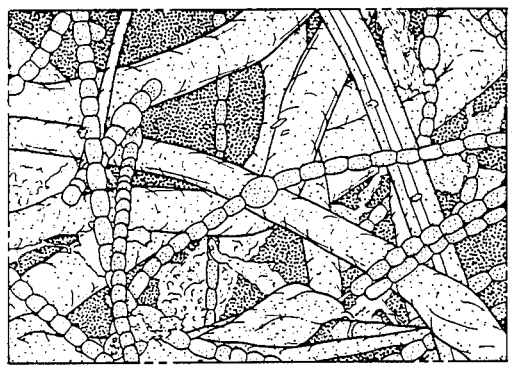
Figure 27:
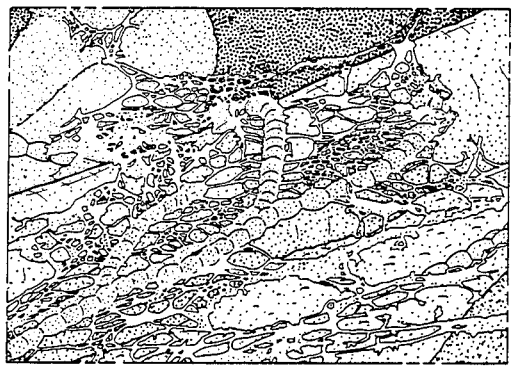
Figure 28:
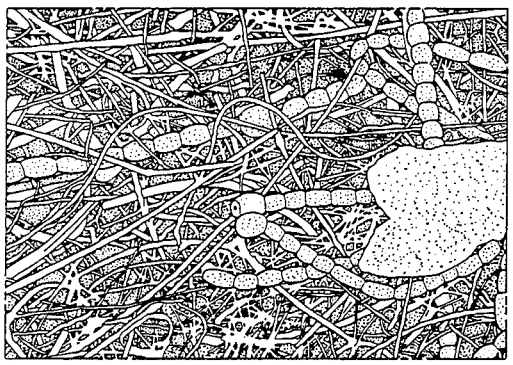
Figure 29:
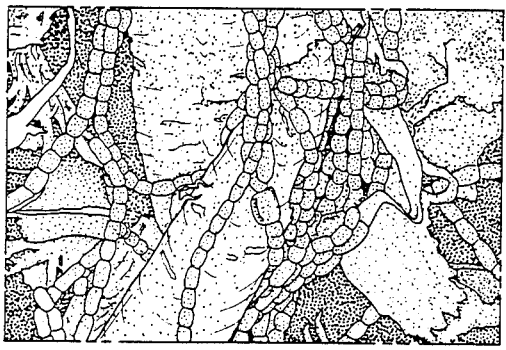
Figures 30A, 30B:
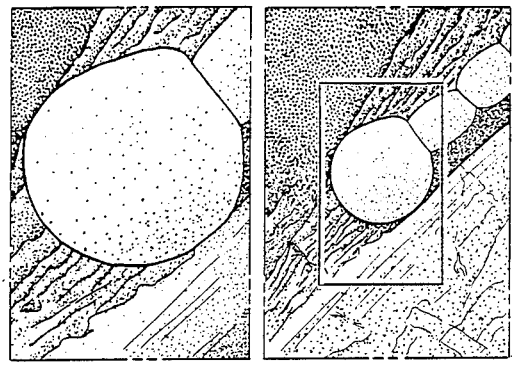
Figure 31:
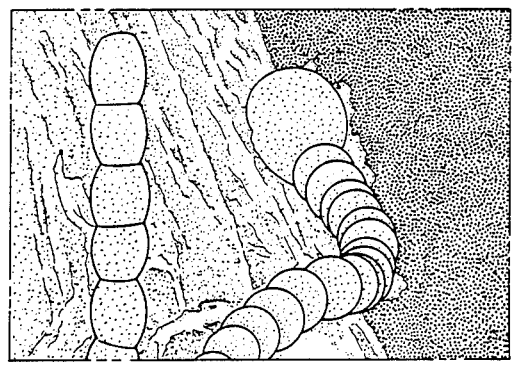
Figure 32:

From Table 14 and FIG. 2, it is evident that the growth for algae immobilized on supports 1 and 3 was less than that of the control, whereas the growth for algae immobilized on support 4 was significantly greater than that of the control. These results may be related to the relative hydrophilicity of each support. Both of supports 1 and 3 are hydrophobic, with support 1 being more hydrophobic (less hydrophilic) than support 3. Support 4, on the other hand, is quite hydrophilic. In the presence of excess water, i.e., in liquid cultures, the hydrophilicity of the support does not appear to have a significant effect on the growth of the immobilized algae (see FIG. 1 and Table 3). In the absence of excess water, a condition which exists for cultures growing on solidified medium, the hydrophilicity of the support seems to be an important factor in the growth of the immobilized algae. That is, the more hydrophilic supports presumably attract and retain moisture which then is available to the algae immobilized thereon.

Such growth on agar-solidified medium also was utilized to demonstrate the ability of the immobilized algae to withstand a dehydration-rehydration cycle without inhibiting or otherwise adversely affecting the ability of the algae to grow and fix nitrogen. It is known that at least some species of blue-green algae are drought resistant or able to become viable upon rewetting after being maintained in a dry state for up to two years; see, for example, D. S. Coxson and K. A. Kershaw, *Can. J. Bot.*, 61, 2658 (1983); and S. Scherer et al., *Oecologia*, 62, 418 (1984). However, nothing is known regarding the drought resistance of immobilized algae.

Algae were immobilized on polypropylene fibers, i.e., support 1, as described above for the growth studies on ASM. The resulting algae/support composite was removed from the liquid culture and allowed to air dry. Samples of the dried composite were allowed to remain in a dehydrated state, but otherwise under normal growth conditions for cultures on ASM, for periods of up to seven days. The samples then were placed on ASM plates and incubated under normal growth conditions for periods of up to seven days. In every case, normal growth was reestablished within two days of rehydration and the cultures were able to grow to the same final density as control cultures not subjected to the dehydration-rehydration cycle. This dehydration-rehydration experiment is shown diagrammatically below.

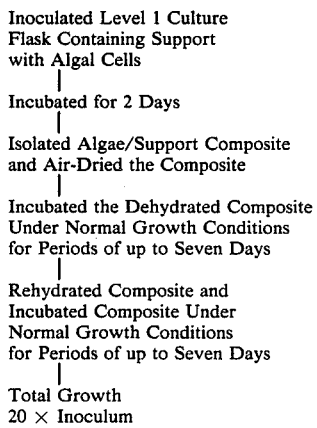

It proved to be a great deal more difficult to accurately measure the nitrogen fixation activity of algae growing on a solid surface with the equipment available. A number of unexpected factors, such as the size of the assay chamber and the gas permeability of the agar-solidified medium, affected the results. Consequently, the variation between replicates typically was of the order of 50 to 80 percent. Nevertheless, it was possible to obtain qualitatively meaningful results.

Algae were immobilized on polypropylene fibers (support 1) in liquid cultures and allowed to grow for one week on both nitrogen-containing and nitrogen-free agar-solidified medium, essentially as described above. At the end of the incubation period, acetylene reduction activity was measured for each composite, followed by the measurement of total chlorophyll. The data thus obtained are summarized in Table 15.

TABLE 15

| Nitrogen-Fixing Activity on Solidified Medium of Algae Immobilized on Polypropylene | | |
|---|---|---|
| Nitrogen Status of ASM | Support Status | Activity[a] |
| Present | Absent | 0.013 |
| Present | Present | 0.018 |
| Absent | Absent | 0.82 |
| Absent | Present | 5.03 |

[a]The average of replicate runs, expressed as micromoles of acetylene reduced per hour per microgram of chlorophyll, times $10^3$.

From the data in Table 15, it is evident that when grown on ASM which contains soluble nitrogen, the algae have negligible nitrogen-fixing activity whether or not the algae are immobilized on a support. When the medium does not contain a nitrogen source, however, considerable nitrogen-fixing activity was observed for both the immobilized algae and the algae which were grown directly on the ASM surface. More importantly, the nitrogen-fixing activity of the immobilized algae was considerably greater than that of the algae growing directly on the ASM surface. While it is not possible to quantitatively compare the two activities, the data suggest that immobilization results in a substantial increase in nitrogen-fixing activity, at least for the support studied.

In an effort to gain some understanding of the immobilization mechanism, many of the algae/support composites obtained from the above experimental studies were analyzed by scanning electron microscopy. All scanning electron microscopy was carried out by Surface Science Laboratories, Inc., Mountain View, Calif. The micrographs were obtained with a Camscan Series 4 Scanning Electron Microscope (Camscan, Cambridge, England). The parameters used were as follows: 60 degree tilt, 15 mm working distance, and 10 keV beam voltage.

Samples were prepared for scanning electron microscopy by Stanford Research Laboratory, Palo Alto, Calif. The protocol employed was as follows: Two or three small squares of sample were placed in a vial to which 3.0 percent by volume cold glutaraldehyde in 0.1 M pH 7.4 phosphate buffer was added. The mixture was allowed to stand for 3-4 hours. The squares then were washed by decanting the glutaraldehyde-containing buffer solution, adding cold freshly made phosphate buffer containing 5.0 percent by weight sucrose for approximately ten minutes, and decanting. This wash procedure was repeated three or four times To the squares of sample then were added 2.0 percent by weight osmium tetraoxide in 0.1 M pH 7.4 phosphate buffer. The resulting mixture was allowed to stand for a minimum of one hour. Dehydration of the sample squares was accomplished by the following sequential additions: cold 50 percent by volume aqueous ethanol for 10-15 minutes, cold 75 percent by volume aqueous ethanol for 10-15 minutes, lukewarm 90 percent by volume aqueous ethanol for 10-15 minutes, three changes of absolute ethanol at ambient temperature for 15 minutes each, and three to four changes of amyl acetate. Critical point drying then was performed using carbon dioxide as the drying liquid.

FIGS. 3-17, inclusive, are reproductions of scanning electron micrographs which are typical of such algae/- support composites, and FIGS. 18-32, inclusive, are hand-drawn representations of the micrographs of FIGS. 3-17, respectively; the micrographs are summarized in Table 16.

TABLE 16
Summary of Scanning Electron Micrographs of Various of the Algae/Support Composites Obtained from the Experimental Studies

| Figures | Support No. | Magnification | Comments |
|---|---|---|---|
| 3/18 | 15 | 4000x | Grown on ASM |
| 4/19 | 17 | 6810x | Grown on ASM |
| 5/20 | 18 | 1550x | Grown in liquid culture |
| 6/21 | 18 | 2410x | Grown in liquid culture |
| 7A/22A | 18 | 1800x | Grown in liquid culture |
| 7B/22B | 18 | 7900x | Grown in liquid culture |
| 8/23 | 18 | 4180x | Grown in liquid culture |
| 9A/24A | 18 | 4150x | Grown in liquid culture |
| 9B/24B | 18 | 18800x | Grown in liquid culture |
| 10/25 | 18 | 9100x | Grown on ASM |
| 11/26 | 21 | 1500x | Grown in liquid culture |
| 12/27 | 21 | 1770x | Grown on ASM |
| 13/28 | 24 | 1690x | Grown in liquid culture |
| 14/29 | 26 | 1770x | Grown in liquid culture |
| 15A/30A | 26 | 6000x | Grown in liquid culture |
| 15B/30B | 26 | 12000x | Grown in liquid culture |
| 16/31 | 26 | 7000x | Grown in liquid culture |
| 17/32 | 26 | 3290x | Grown On ASM |

Remarkably, the algae appear to be attached to the fibers of the supports by means of the heterocysts only. While the vegetative cells clearly are present, they appear to be pendent from the attached heterocyst and occasionally are wrapped about the fiber. Moreover, the attached heterocyst appears to have secreted a substance, possibly a mucoprotein, which serves as the adhesive which binds the heterocyst to the fiber.

Since the heterocyst binds the algae to the support, the reason why algae grown in a nitrogen-rich environment did not attach to the support is now apparent. It also is to be expected that vegetative cells can break off of attached algae since the vegetative cells are not bound to the support. However, the reason for enhanced nitrogen fixation activities with immobilized algae is not clear. Immobilization may alter the metabolism of the attached heterocysts. It also is possible that immobilization through the heterocysts effectively increases the ratio of heterocysts to vegetative cells relative to algae growing in suspension.

CONCLUSIONS ON ATTACHMENT, GROWTH, AND NITROGEN FIXATION

From the results obtained thus far, several conclusions can be drawn:

(1) filamentous heterocystous blue-green algae in nitrogen-poor liquid cultures attach readily to supports, the extent of attachment being directly proportional to the surface energy of the support, i.e., the greater the surface energy, the greater the extent of attachment;

(2) the algae attach to the supports by means of the heterocysts, attachment being accomplished by a substance apparently secreted by the heterocysts;

(3) in liquid cultures, algae immobilized on supports grow at least as well as algae grown in suspension;

(4) in liquid cultures, algae immobilized on supports exhibit significantly enhanced nitrogen-fixation activity relative to algae in suspension;

(5) on agar-solidified medium, the growth of algae immobilized on supports is dependent upon the hydrophilicity of the support, i.e., the more hydrophilic the support, the better the growth;

(6) on agar-solidified medium, the growth of algae immobilized on the more hydrophobic (or less hydrophilic) supports is somewhat less than that of algae growing directly on the medium, whereas the growth of algae immobilized on a very hydrophilic support is significantly better than that of algae growing directly on the medium; and (7) on agar-solidified medium, algae immobilized on a very hydrophilic support exhibit substantially enhanced nitrogen-fixation activity relative to algae growing directly on the medium.

As noted earlier, many substances in the past have been immobilized on substantially water-insoluble supports. These substances include enzymes, antigens, antibodies, binding proteins for such substances as antibodies and enzymes, and various microorganisms. The best that typically was hoped for as a result of such immobilization was that the activity or characteristic of interest remained relatively unchanged as a consequence of the immobilization procedure. Frequently, however, immobilization resulted in a substantial or complete loss of the desired activity or characteristic. Consequently, a high degree of unpredictability has been associated with most immobilization procedures, especially those applied to unexplored areas. Thus, the immobilization of blue-green algae described herein is truly remarkable.

GREENHOUSE STUDIES

Having established that blue-green algae attach to a wide variety of supports and that the attached algae are capable of both growing and fixing nitrogen, greenhouse studies were carried out to demonstrate that the attached or immobilized algae were capable of serving as a nitrogen fertilizer under essentially natural growing conditions.

These studies were carried out in the greenhouse facility of Iowa State University; Ames, Iowa. The temperature within the greenhouse was maintained at approximately 80 degrees F. (approximately 27 degrees C.) and the plants were subjected to natural light conditions.

A series of growth experiments was designed to measure the effect of blue-green algae on the growth of tomato seedlings in sand. Tomato plants were chosen as the test plants because the seeds germinate well in sand and the plants grow rapidly as seedlings and are known to require nitrogen for normal development.

The experiments were carried out in flats filled with sterilized greenhouse sand. Sand was used as an inert support and all nutrients were supplied to the plants in the form of a liquid fertilizer. This was done to insure, to the greatest extent possible, that all nutrients available to the plants, including minerals and trace elements, were supplied only in controlled amounts by the fertilizer solution. In all experiments, the flats were watered with equal volumes of fertilizer solution, either with or without soluble nitrogen, depending upon the particular experiment. The composition of the fertilizer solution was the same as the algal growth medium described earlier and summarized in Table 1 at pages 17 and 18.

These experiments also were designed to test the efficacy of support 4 as a carrier for the algae in field use. Since it was not practical to test all of the supports examined in the experimental studies, support 4 was selected for the greenhouse studies because of the exceptional growth and nitrogen-fixation activity observed with the algae/support composite on agar-solidified medium.

The amount of algal material deemed appropriate for each flat was 6 g (wet weight). An effort was made to keep the number of algal cells applied to each flat essentially constant. For application, the algal mass was resuspended in a volume of the appropriate medium which was one-fourth of the initial volume used to water the flats. The remaining volume was applied in the form of the medium used to resuspend the cells.

For those experiments requiring support, the level per flat selected was 400 ml of dry, unpacked support which was sufficient to cover the entire surface of the sand in the flat. Plant growth was measured by determining the height and weight of each plant after 2.5-3 weeks of growth; the growth period included germination time. The flats were checked daily and watered as needed with the appropriate fertilizer solution (with or without nitrogen). As already mentioned, the volume of liquid applied to each flat was the same.

In the first experiment, tomato seeds were sprinkled over the surface of each of two flats. One was watered with fertilizer solution containing nitrogen and the other was watered with nitrogen-free fertilizer solution. After three weeks of growth, the plants were harvested and the height and weight of each was measured. An average height and weight then were calculated. The results are summarized in Table 17.

TABLE 17

Effect of Nitrogen on Growth of Tomato Plants

| Nitrogen Status | Average Height, cm | Average Weight, g |
|---|---|---|
| Present | 3.5 ± 0.6 | 0.188 ± 0.045 |
| Absent | 2.0 ± 0.4 | 0.051 ± 0.014 |

The growth of tomato seedlings clearly is nitrogen-dependent, verifying the utility of the plant for studying the efficacy of immobilized algae as a nitrogen fertilizer.

In the next experiment, two flats were filled with sand and planted with tomato seeds in furrows approximately three inches (approximately 7.6 cm) apart. Both flats were covered with a layer of support 4. A suspension of algal cells in nitrogen-free medium was distributed over one flat. An equal volume of the nitrogen-medium was distributed over the other flat. Both flats were watered with nitrogen-free medium for the duration of the experiment. At the end of the three-week growth period, algae were observed to be growing on the support in the algae-inoculated flat, indicating that the cells were able to survive on the surface for at least that period of time. The plants were harvested, measured, and weighed as before, with the results shown in Table 18.

TABLE 18

Effect of Algae on Growth of Tomato Plants in Presence of Support 4

| Algae Status | Average Height, cm | Average Weight, g |
|---|---|---|
| Absent | 2.0 ± 0.3 | 0.037 ± 0.011 |
| Present | 3.7 ± 0.6 | 0.133 ± 0.037 |

The plants grown in the presence of algae and support 4, i.e., the algae/support 4 composite, appeared to be developing much more rapidly than the plants grown in the absence of such composite, and had good primary leaf development at the time of harvesting.

The effect of support 4 on plant growth was evaluated next. Two flats were prepared as described above. One was covered with a layer of support 4 and both were watered with equal volumes of nitrogen-containing medium. After a three-week growth period, the same harvesting and measuring procedure was followed. The results are shown in Table 19.

TABLE 19

Effect of Support 4 on Growth of Tomato Plants

| Support Status | Average Height, cm | Average Weight, g |
|---|---|---|
| Absent | 3.6 ± 0.5 | 0.193 ± 0.038 |
| Present | 3.4 ± 0.5 | 0.185 ± 0.053 |

When used alone, support 4 appears to have a slightly detrimental, but statistically insignificant, effect on plant growth and development.

The foregoing greenhouse experiments demonstrated that the model selected is useful in assessing the effects of algae and support 4 on plant growth. However, the experiments described thus far were done at different times. Because of varying weather conditions, such as outside temperature, cloud cover, humidity, and the like, it is not possible to directly compare results from one experiment with those of another. Consequently, the growth studies were repeated in an experiment which involved simultaneously testing all of the variables studied thus far.

Four pairs of flats were prepared and planted with tomato seeds as described above. One pair was covered with support 4 only, one pair with algae only, and one pair with support and algae. In each pair, one flat was watered only with nitrogen-containing medium and the other was watered with nitrogen-free medium. The growth period was three weeks, after which time the usual harvesting and measuring procedures were carried out. In addition, germination rates were estimated, recorded as the percentage of seeds germinating and growing as seedlings. A summary of flat preparation is given in Table 20, and the results are presented in Table 21:

TABLE 20

Summary of Flat Preparation

| Flat Designation | Nitrogen Status | Support Status | Algae Status |
|---|---|---|---|
| IA | Present | Absent | Absent |
| IB | Absent | Absent | Absent |
| IIA | Present | Present | Absent |
| IIB | Absent | Present | Absent |
| IIIA | Present | Absent | Present |
| IIIB | Absent | Absent | Present |
| IVA | Present | Present | Present |
| IVB | Absent | Present | Present |

TABLE 21

Summary of Results

| Flat Designation | Germination Rate, % | Average Height, cm | Average Weight, g |
|---|---|---|---|
| IA | 62 | 2.4 ± 0.6 | 0.151 ± 0.040 |
| IB | 56 | 1.5 ± 0.3 | 0.036 ± 0.010 |
| IIA | 64 | 2.4 ± 0.4 | 0.120 ± 0.036 |
| IIB | 53 | 1.6 ± 0.4 | 0.022 ± 0.007 |
| IIIA | 56 | 2.2 ± 0.6 | 0.112 ± 0.044 |
| IIIB | 60 | 2.3 ± 0.4 | 0.103 ± 0.039 |
| IVA | 62 | 2.7 ± 0.5 | 0.127 ± 0.037 |

TABLE 21-continued

| Flat Designation | Summary of Results | | |
|---|---|---|---|
| | Germination Rate, % | Average Height, cm | Average Weight, g |
| IVB | 67 | 3.2 ± 0.4 | 0.170 ± 0.051 |

The variation observed for germination rate is not seen as having great significance, although it is interesting to note that, even with such variation, the germination rate for flat IVB was the highest. Moreover, the higher growth rates within pairs consistently were observed for flats having the higher germination rates.

With respect to the growth data, weight is believed to be the more accurate measure of total plant development because in the very early stages of growth, leaf development and expansion are favored over stem elongation. Both parameters, however, clearly demonstrate the efficacy of the algae/support 4 composite in supporting the growth of tomato seedlings. Furthermore, the composite was significantly more effective than algae alone. This probably is a reflection of the higher nitrogen-fixation rates observed with the composite when grown on the agar-solidified medium. It perhaps should be noted that the composite also served to limit erosion of the sand surface during the watering process.

Having thus described the invention, numerous modifications will become apparent to those having ordinary skill in the art without departing from either the spirit or the scope thereof.

What is claimed is:

1. A composite which comprises a substantially water-insoluble support having a surface energy of from about 30 dynes per cm to about 115 dynes per cm to which nitrogen-fixing filamentous blue-green algal heterocyst cells are attached, said support being polypropylene or a cellulosic which is particulate or fibrous and which is substantially free of substances which have a significant deleterious effect on the viability of the attached algae, which attached algal heterocyst cells, when allowed to grow in nitrogen-deficient environment, fix nitrogen at a rate which is substantially greater than that of such cells not so attached.

2. The composite of claim 1, in which said polypropylene support is meltblown.

3. The composite of claim 1, in which said cellulosic support comprises thermomechanical wood pulp.

4. The composite of claim 1, in which said cellulosic support is debonded chemical wood pulp.

5. The composite of claim 1 in admixture with water.

6. The composite of claim 3 in admixture with water.

7. The composite of claim 4 in admixture with water.

* * * * *

UNITED STATES PATENT AND TRADEMARK OFFICE
CERTIFICATE OF CORRECTION

PATENT NO. : 4,921,803

DATED : May 1, 1990

INVENTOR(S) : Ronald S. Nohr

It is certified that error appears in the above-identified patent and that said Letters Patent is hereby corrected as shown below:

Column 1, line 45, "Tonoxun" should read --Tongxun--; line 59, "Can. . Microbiol.," should read --Can. J. Microbiol.,--; line 64, "Aool." should read --Appl.--;

Column 2, line 5, "Conor." should read --Congr.--;

Column 5, line 42, "Scytonematacea" should read --Scytonemataceae--;

Column 6, lines 37-38, "derived" should read --derived through gene splicing and/or cell fusion techniques.--;

Column 10, line 57, "No. 085713" should read --No. 08-75713--;

Column 16, line 61, "percent" should read --80 percent--;

Column 18, line 46, "given one" should read --given, one--; line 52, "Alis" should read --Allis--;

UNITED STATES PATENT AND TRADEMARK OFFICE
CERTIFICATE OF CORRECTION

PATENT NO.  : 4,921,803

DATED       : May 1, 1990

INVENTOR(S) : Ronald S. Nohr

It is certified that error appears in the above-identified patent and that said Letters Patent is hereby corrected as shown below:

Column 25, line 29, "fabric type" should read --fabric-type--;

Column 29, line 39, "cultures" should read --cultures)--; line 68, "was..." should read --was necessary to develop techniques for determining both growth and nitrogen-fixation rates for algal cells grown on solidified medium and to use such techniques to determine the properties of algae immobilized on the surfaces of various supports.--; and Column 32, line 53, "times To" should read --times. To--.

Signed and Sealed this

Eighteenth Day of May, 1993

Attest:

MICHAEL K. KIRK

Attesting Officer      Acting Commissioner of Patents and Trademarks